US007579487B2

(12) United States Patent
Dreher et al.

(10) Patent No.: US 7,579,487 B2

(45) Date of Patent: Aug. 25, 2009

(54) PROCESS FOR MAKING N-SULFONATED-AMINO ACID DERIVATIVES

(75) Inventors: Spencer D. Dreher, Metuchen, NJ (US); Norihiro Ikemoto, Edison, NJ (US); C. Scott Shultz, Maplewood, NJ (US); J. Michael Williams, Hillsborough, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 11/578,283

(22) PCT Filed: May 6, 2005

(86) PCT No.: PCT/US2005/015770

§ 371 (c)(1),
(2), (4) Date: Oct. 12, 2006

(87) PCT Pub. No.: WO2005/118529

PCT Pub. Date: Dec. 15, 2005

(65) Prior Publication Data

US 2007/0219382 A1 Sep. 20, 2007

Related U.S. Application Data

(60) Provisional application No. 60/569,997, filed on May 11, 2004.

(51) Int. Cl.
*C07D 309/06* (2006.01)

(52) U.S. Cl. .................................................... 549/426

(58) Field of Classification Search .................. 549/426
See application file for complete search history.

(56) References Cited

U.S. PATENT DOCUMENTS

| | | | |
|---|---|---|---|
| 4,962,230 | A | 10/1990 | Takaya et al. |
| 5,239,078 | A | 8/1993 | Galardy et al. |
| 5,478,820 | A | 12/1995 | Betts et al. |
| 5,559,267 | A | 9/1996 | Burk |
| 5,591,631 | A | 1/1997 | Leppla et al. |
| 5,677,274 | A | 10/1997 | Leppla et al. |
| 5,712,300 | A | 1/1998 | Jacobsen |
| 5,773,438 | A | 6/1998 | Levy et al. |
| 5,804,593 | A | 9/1998 | Warpehoski et al. |
| 5,863,949 | A | 1/1999 | Robinson et al. |
| 5,892,112 | A | 4/1999 | Levy et al. |
| 6,022,893 | A | 2/2000 | Sakai et al. |
| 6,143,744 | A | 11/2000 | Broka et al. |
| 6,150,394 | A | 11/2000 | Watanabe et al. |
| 6,218,389 | B1 | 4/2001 | Almstead et al. |
| 6,225,311 | B1 | 5/2001 | Levin et al. |
| 6,277,987 | B1 | 8/2001 | Kukkola et al. |
| 6,803,379 | B2 | 10/2004 | Fernandez-Pol et al. |
| 6,893,835 | B2 | 5/2005 | Duesbery et al. |
| 6,911,203 | B2 | 6/2005 | Duesbery et al. |
| 6,927,068 | B2 | 8/2005 | Simonson et al. |
| 6,979,449 | B1 | 12/2005 | Mock |
| 2003/0224403 | A1 | 12/2003 | Popov et al. |
| 2004/0006040 | A1 | 1/2004 | Schechter |
| 2004/0076638 | A1 | 4/2004 | Siloach et al. |
| 2004/0138103 | A1 | 7/2004 | Patt |
| 2004/0235136 | A1 | 11/2004 | Singh et al. |
| 2005/0085504 | A1 | 4/2005 | Nelson et al. |
| 2005/0113344 | A1 | 5/2005 | Li et al. |
| 2005/0148629 | A1 | 7/2005 | Xiong et al. |
| 2005/0287074 | A1 | 12/2005 | Carpenter et al. |
| 2006/0084688 | A1 | 4/2006 | Barta et al. |
| 2006/0246532 | A1 | 11/2006 | Frucht et al. |
| 2007/0027064 | A1 | 2/2007 | Appelbaum |
| 2007/0054861 | A1 | 3/2007 | Rougeot et al. |
| 2007/0117848 | A1 | 5/2007 | Puerta et al. |
| 2007/0142318 | A1 | 6/2007 | Sonenshein |

FOREIGN PATENT DOCUMENTS

| | | | |
|---|---|---|---|
| EP | 178 911 | B1 | 1/1992 |
| EP | 0 950 656 | B1 | 2/1999 |
| EP | 1 069 110 | A1 | 1/2001 |
| EP | 757 984 | B1 | 10/2002 |
| EP | 1 486 207 | A3 | 12/2004 |
| JP | 10-204059 | A | 8/1998 |
| JP | 11-035557 | A | 2/1999 |
| JP | 11-501910 | A | 2/1999 |
| JP | 11-246527 | A | 9/1999 |
| JP | 2001-503400 | A | 3/2001 |
| JP | 2001-513484 | A | 8/2001 |
| WO | WO 96/27583 | A1 | 9/1996 |
| WO | WO 97/05865 | A1 | 2/1997 |
| WO | WO 97/27174 | A1 | 7/1997 |
| WO | WO 98/17645 | A1 | 4/1998 |
| WO | WO 98/18754 | A1 | 5/1998 |
| WO | WO 98/39329 | A1 | 9/1998 |
| WO | WO 98/42659 | A2 | 10/1998 |
| WO | WO 99/04780 | A1 | 2/1999 |
| WO | WO 99/06340 | A2 | 2/1999 |

(Continued)

OTHER PUBLICATIONS

R. J. Cherney et al., "Desing, Syntesis, and Evaluation of Benzothiadiazepine Hydroxamates as Selective Tumor Necrosis Factor—alpha Converting Enzyme Inhibitors", 2003, pp. 1811-1823, vol. 46, J. Med. Chem.

(Continued)

*Primary Examiner*—Taofiq A Solola
(74) *Attorney, Agent, or Firm*—Julie M. Lake; Sheldon O. Heber

(57) ABSTRACT

This invention relates to a process for preparing optically active α-amino acid substrates which are used to make potent lethal factor (LF) inhibitors for the treatment of anthrax. This invention further relates to a process for synthesis of potent LF-inhibitors for the treatment of anthrax. Specifically, the invention concerns a novel, high-yielding and highly enantioselective asymmetric hydrogenation reaction of a tetrasubstituted ene-sulfonamide acid or ester.

4 Claims, No Drawings

FOREIGN PATENT DOCUMENTS

| | | | |
|---|---|---|---|
| WO | WO 99/42443 | A1 | 8/1999 |
| WO | WO 99/50439 | A2 | 10/1999 |
| WO | WO 99/52889 | A1 | 10/1999 |
| WO | WO 99/57097 | A2 | 11/1999 |
| WO | WO 99/58947 | A2 | 11/1999 |
| WO | WO 00/15213 | A1 | 3/2000 |
| WO | WO 01/70690 | A1 | 9/2001 |
| WO | WO 02/072577 | A2 | 9/2002 |
| WO | WO 03/035610 | A1 | 5/2003 |
| WO | WO 03/051825 | A1 | 6/2003 |
| WO | WO 03/073066 | A2 | 9/2003 |
| WO | WO 03/101382 | A2 | 12/2003 |
| WO | WO 2004/011449 | | 2/2004 |

OTHER PUBLICATIONS

J. Inoue et al., "Structure-Activity Relationship Study and Drug Profile of N-(4-Fluorophenylsulfonyl)-L-valyl-l-leucinal (SJA6017) as a Potent Calpain", 2003, pp. 868-871, vol. 46, J. Med. Chem.
H. B. Milne et al., "The use of N-Benzylsulfonyl-alpha-amino Acids in Enzymatic Syntheses of the L-Phenylhydrazides, and for Enzymatic Resolutions", 1957, pp. 645-648, vol. 79, J. Amer. Chem. Soc.
T. Benincori et al., "2.2, 5.5-Tetramethyl-4,4'-bis (diphenylphoshino)3.3-Bithiphene: A New, Very Efficent, Easily Accessible, Chiral Biheteroaromatic Ligand for Homogeneous Steroselective Catalysis", 2000, pp. 2043-2047, vol. 65, J. Org. Chem.
D. Liu et al., "A Novel Chiral Ferrocenyl Phosphine Ligand from Sugar: Applications in Rh-Catalyzed Asymmetric Hydrogenation Reactions", 2002, pp. 4471-4474, vol. 4, Organic Letters.
A. Togni et al., "A Novel Easily Accessible Chiral Ferroncenyldiphosphine for Highly Enantioselective Hydrogenantion, Allylic Alkylation, and Hydroboration Reactions", 1994, pp. 4062-4066, vol. 116, J. Am. Chem. Soc.
K. Mashima et al., "Synthesis of New Cationic BINAP-Ruthenium(II) Complexes and Their Use in Asymmertic Hydrogenation [BINAP-2,2' bis(Diphenylphosphino)-1,1'-binaphthyl]", 1989, pp. 1208-1210, J. Chem. Soc. Chem Comm.
H. Takaya et al., "New Chiral Ruthenium Complexes for Asymmetric Catalytic Hydrogenations" 1990, pp. 1135-1138, vol. 62, Pure & Appl. Chem.
U.S. Appl. No. 11/006,335, Hermes (unpublished).
Daniel P. Becker et al., 11 Bioorganic & Medicinal Chemistry Letters 2719-25 (2001).
John M. Clements et al., 46(6) Antimicrobial Agents & Chemotherapy 1793-99 (2002).
Terry C. Dixon et al., 341(11) The New England Journal of Medicine 815-20 (1999).
David J. Weber et al., 32(5) Antimicrobial Agents & Chemotherapy 642-45 (1988).
Erlendur Helgason et al., 66(6) Applied & Environmental Microbiology 2627-30 (2000).
Mehmet Doganay et al., 23 Scand. J. Infect. Dis. 333-35 (1991).
Andrea Scozzafava & Claudiu T. Supuran, 43(20) J. Med. Chem. 3677-87 (2000); Correction: 44(6) J. Med. Chem. 1016 (2001).
Michele Mock & Agnes Fouet, 55 Annual Review of Microbiology 647-71 (2001).
Gaetano Vitale et al., 248(3) Biochem. Biophys. Res. Commun. 706-11(1998).
Gaetano Vitale et al., 352 Biochem. J. 739-45 (2000).
Nicholas S. Duesbery et al., 280 Science 734-37 (1998).
S.E. Hammond & P.C. Hanna, 66(5) Infect. Immun. 2374-78 (1998).
Ansu Agrawal et al., 424 Nature 329-34 (2003).
Richard T. Cummings et al., 99(10) PNAS 6603-06 (2002).
Paolo Ascenzi et al., 5531 FEBS Letters 384-88 (2002).
Sharon M. Dankwardt et al., 11(16) Bioorganic & Medicinal Chemistry Letters 2085-88 (2001).
Stanislaw Pikul et al., 44(16) J. Med. Chem. 2499-2502 (2001).
Minoru Ikeda et al., 6(8) Clinical Cancer Research 3290-96 (2000).
Patrick M. O'Brien et al., 43(2) J. Med. Chem. 156-66 (2000).
G. Vidyasagar Reddy et al., 29(20) Synthetic Communications 3613-19 (1999).
Tom Brennan et al., 61(1) Biotechnology & Bioengineering 33-45 (1998).
Yoshinori Tamura et al., 41(4) J. Med. Chem. 640-49 (1998).
Jan-Gerd Hansel et al., 36(17) Tetrahedron Letters 2913-16 (1995).
Samuel Natelson & Ethan Natelson, 40(2) Microchemical Journal 226-32 (1989).
Naoto Yoneda et al., 89(1) Yakugaku Zasshi 98-103 (1969).
Armelle Menard et al., 320 Biochem. J. 687-91 (1996).
W.L. Shoop et al., 102(22) PNAS (2005).
Donald Clark Wetter et al., 91(5) Am. J. Pub. Health 710-16 (2001).
Sshirin Shafazand et al., 116 CHEST 1369-76 (1999).
Advisory Action dated May 6, 2008, in U.S. Appl. No. 11/006,335.
Amendment filed Jul. 15, 2008, with Request for Continued Examination, in response to May 6, 2008, Advisory Action in U.S. Appl. No. 11/006,335.
Notice of Allowance dated Apr. 18, 2008, in U.S. Appl. No. 10/509,972.
Amendment filed Jul. 15, 2008, with Request for Continued Examination, in response to Notice of Allowance dated Apr. 18, 2008, in U.S. Appl. No. 10/509,972.
C. Scott Shultz et al., 7(16) Org. Lett. 3405-08 (2005).

PROCESS FOR MAKING N-SULFONATED-AMINO ACID DERIVATIVES

This Application claims the benefit of U.S. Provisional Application 60/569,997, filed May 11, 2004.

BACKGROUND OF THE INVENTION

Asymmetric hydrogenation of dehydro-α-amino acid derivatives is a very widely used transformation in the pharmaceutical and fine chemicals industries. Rhodium catalysts containing chiral bisphosphine ligands provide ready access to these valuable synthetic targets with chiral purities routinely >95% ee, often with S/C ratios exceeding $10^4$. For optimal hydrogenation performance, dehydro-amino acid substrates are typically protected as the enamide.

This invention relates to sulfonamide derived amino acid substrates for asymmetric hydrogenation utilizing rhodium, ruthenium and iridium metal catalysts. Processes for making N-sulfonamide α-amino acid derivatives from naturally occurring amino acids are disclosed in Cherney, Robert J. et al., J Med. Chem. (2003), 46(10), 1811-1823 and Inoue, Jun, et al., J. Med. Chem. (2003), 46(5), 868-871. Synthesis of N-sulfonamide amino acids via enzymatic methods is disclosed in Milne, H. Bayard, et al., J. Amer. Chem. Soc. (1957), 79, 645-648 and WO 2004/011449 (Wosikowski-Buters, Katja, et al.). See also U.S. Pat. No. 4,962,230, which discloses a process for making optically active carboxylic acids. See also U.S. Pat. No. 5,559,267.

More particularly, this invention relates to a process for preparing optically active α-amino acid derivatives which can be employed to make N-sulfonamide compounds that are useful against anthrax and/or for inhibiting lethal factor. This invention also relates to an efficient and scaleable synthesis for making lethal factor inhibitors for the treatment of anthrax infection. The N-sulfonamide compounds of this invention are disclosed in PCT patent application US03/16336 and U.S. patent application 60/530103, both herein incorporated by reference in their entirety.

SUMMARY OF THE INVENTION

This invention relates to a process for preparing optically active α-amino acid substrates which are used to make potent lethal factor (LF) inhibitors for the treatment of anthrax. This invention further relates to a process for synthesis of potent LF-inhibitors for the treatment of anthrax. This invention further relates to a sulfonamide protected hydrogenation of dehydro amino acids utilizing ruthenium catalysts. Specifically, the invention concerns a novel, high-yielding and highly The process provides LF inhibitors with a minimum purity of 98 % with maximum 0.5% individual impurity and maximum undesired enantiomer of 0.5%. Heavy metals are less than 10 ppm. Optically active α-amino acid derivatives, which are sulfonated at nitrogen in one step using a chiral metal catalyst-phosphine ligand complex are also described in this process. Particularly, the invention relates to a process for making an optically active sulfonamide compound of formula I or Ia:

Formula I

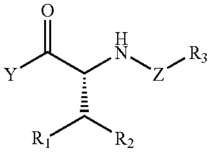

or

Formula Ia

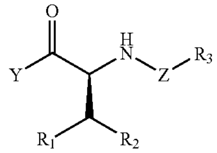

or a pharmaceutically acceptable salt, enantiomer, diastereomer or in vivo hydrolysable ester or mixture thereof, wherein, $R^3$ represents $(CH_2)_nC_{6-10}$ aryl, $(CH_2)_nC_{5-10}$ heteroaryl or $(CH_2)_nC_{5-10}$ heterocyclyl, $O(CH_2)_nC_{5-10}$ heterocyclyl, said aryl, heteroaryl and heterocyclyl optionally substituted with 1 to 3 groups of $R^a$ $R^a$ represents $C_{1-6}$ alkyl, halogen, OH, aryl($C_{1-6}$)alkyl, ($C_{1-6}$) alkoxy, ($C_{1-6}$)alkoxy($C_{1-6}$)alkyl, halo($C_{1-6}$)alkyl, nitro, amino, mono- or di-N—($C_{1-6}$)alkylamino, acylamino, acyloxy, carboxy, carboxy salts, carboxy esters, carbamoyl, mono- and di-N—($C_{1-6}$)alkylcarbamoyl, ($C_{1-6}$)alkoxycarbonyl, aryloxycarbonyl, ureido, guanidino, sulphonylamino, aminosulphonyl, ($C_{1-6}$)alkylthio, ($C_{1-6}$)alkylsulphinyl, ($C_{1-6}$)alkylsulphonyl, heterocyclyl, heterocyclyl ($C_{1-6}$)alkyl; and Z represents C═O or $S(O)_2$;

Y represents $OR_4$, or NHOH;

$R_4$ represents H or $C_{1-4}$ alkyl;

n is 0 to 4;

$R_1$ and $R_2$ independently represents hydrogen, $C_{6-10}$ aryl, or $C_{1-8}$ alkyl, or $R_1$ and $R_2$ combined represent $C_{3-10}$ cycloalkyl, $C_{3-10}$ heterocycloalkyl, $C_{6-10}$ aryl, or $C_{5-11}$ heterocyclyl, said aryl and heterocyclyl optionally substituted with 1 to 3 groups of $R^a$ and said alkyl, optionally substituted with 1-3 groups selected from the group consisting of $C_{1-6}$ alkyl, $C_{1-6}$ alkoxy, $C_{6-10}$ aryl, halogen, carbonyl, or direct heteroatom attachment, comprising asymmetrically hydrogenating a compound of formula II:

Formula II

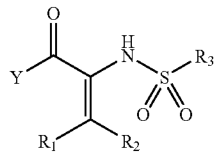

in the presence of a metal catalyst and a ligand to produce a compound of formula I, wherein $R_1$, $R_2$ and $R_3$ are described herein.

This and other aspects of the invention will be realized upon inspection of the invention as a whole.

DETAILED DESCRIPTION OF THE INVENTION

The invention is described herein in detail using the terms defined below unless otherwise specified.

When any variable (e.g. aryl, heterocycle, $R^1$, R etc.) occurs more than one time in any constituent, its definition on each occurrence is independent at every other occurrence. Also, combinations of substituents/or variables are permissible only if such combinations result in stable compounds.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopentyl and cyclohexyl. When the alkyl group is said to be substituted with an alkyl group, this is used interchangeably with "branched alkyl group".

Preferably, alkenyl is $C_2$-$C_6$ alkenyl.

Preferably, alkynyl is $C_2$-$C_6$ alkynyl.

Cycloalkyl is a specie of alkyl containing from 3 to 15 carbon atoms, unless otherwise specified, without alternating or resonating double bonds between carbon atoms. It may contain from 1 to 4 rings that are fused. Examples of cycloalkyl groups are cyclopropyl, cyclobutyl, cyclopentyl, cyclohexyl, and cycloheptyl. Heterocycloalkyl is intended to mean cycloalkyl ring groups which consists of carbon atoms and from one to four heteroatoms selected from the group consisting of N, O, and S, and including any bicyclic. Said heterocycloalkyl can optionally be substituted with 1 to 3 groups of $R^a$ described herein. Examples of Heterocycloalkyls are oxane, methyloxane, dioxane, pyran, thiolane, piperidine, pyrrolidine, aziridine, azetidine, etc.

Alkoxy refers to $C_1$-$C_6$ alkyl-O—, with the alkyl group optionally substituted as described herein. Examples of alkoxy groups are methoxy, ethoxy, propoxy, butoxy and isomeric groups thereof.

Halo is short for halogen and refers to chloride, fluoride, bromide and iodide.

As used herein, "aryl" is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocyclyl or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. A fused heterocyclic ring system may include carbocyclic rings and need include only one heterocyclic ring. The term heterocycle or heterocyclic includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl and triazolyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzofuranyl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, thienyl and triazolyl.

This invention also relates to a process for making a compound of Formula III, Formula IIIa or mixture thereof:

Formula III

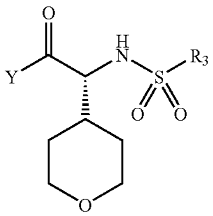

or

Formula IIIa

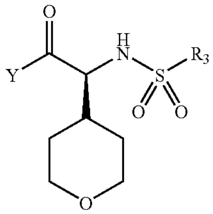

a pharmaceutically acceptable salt or mixture thereof, comprising (1) reacting the compound of formula IV Formula IV

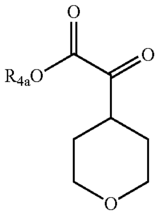

with compound of formula V

Formula V

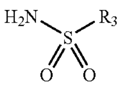

in the presence of an acid such as methanesulfonic acid, pTsOH, CSA, $PhSO_3H$, phosphoric acids, TFA, AcOH, $H_2SO_4$ and HCl; acidic reagents such as $POCl_3$ and the like are also effective, (2) heating to a temperature of about 100° C. to about 125° C., preferably about 105° C. to about 117° C. for about one to about 30 hours, preferably about 12 to about 28 hours, to produce a compound of formula VI;

Formula VI

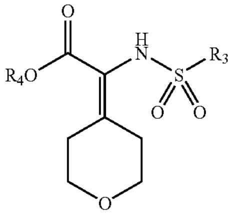

(3) asymmetrically hydrogenating a compound of formula VI in the presence of a metal catalyst and ligand to produce a compound of formula III, IIIa, or mixture thereof, wherein $R_3$ and $R_4$ are as described herein, Y represents $OR_4$ or NHOH; and $R_{4a}$ represents H, $C_{1-4}$ alkyl, magnesium, lithium, sodium, or potassium and wherein Y is NHOH only after further derivation as shown herein.

The reaction of combining the compounds of formula IV and V is generally conducted using solvents such as toluene, benzene, heptane, hexane, THF and acetonitrile. When solvents such as toluene are used high-boiling co-solvents such as diethylene glycol diethylether or a solubilizing solvent such as DMAc or DMF can be added. After step (2) the reaction can be cooled to a temperature of about 10° C. to about 1° C. before conducting step (3).

One embodiment of this invention is realized when the ligand is a chiral monodentate or polydentate, which optionally can possess an alkylated or arylated phosphine. Examples of ligands are TetraMe-BITIOP-(TMBTP—see Benincori, T.; Cesarotti, E.; Piccolo, O.; Sannicolo, F. J. Org. Chem., 2000, 65, 2043-2047 for full name); (S)-Me-f-Ketalphos-((3aS,3'aS,4S,4'S,6S,6'S, 6aS,6'aS)-5,5'-[1,1'-ferrocenyl]bis[tetrahydro-2,2,4,6-tetramethyl-4H-phospholo[3,4-d]-1,3-dioxole] see Liu, D.; Li, W.; Zhang, X. Organic Letters, 2002, 4, 4471-4474); (S)-BINAP; (R,R)-Et-ferrotane; (R)-xylBINAP; (R)-phanephos; (S)-Binaphane; (R)-xylPhanephos; (R,S)-Tangphos; (S)-Me-BoPhoz; (S,S)-Norphos; (R,R)-Me-DuPhos; (R)-(S)-((diphenylphosphino) ferrocenyl-ethyldicyclohexylphosphine); ((R)-(S)-((diphenylphosphino)ferrocenyl-ethyldi-t-butylphosphine) see Togni, A.; Breutel, C.; Schnyder, A.; Spindler, F.; Landert, H.; Tijani, A. J. Am. Chem. Soc., 1994, 116, 4062-4066); (R,S)-((di-t-butylphosphino)ferrocenyl-ethyldi-3,5-dimethylphenylphosphine); (S)-(R)-((diphenylphosphino)ferrocenyl-ethyldicyclohexylphosphine), ((S)-(R)-((diphenylphosphino)ferrocenyl-ethyldi-t-butylphosphine)), and (S)-(R)-((di-t-butylphosphino)ferrocenyl-ethyldi-3,5-dimethylphenylphosphine) preferably (R)-(S)-((diphenylphosphino)ferrocenyl-ethyldi-t-butylphosphine or (−)-TMBTP. (−)-TMBTP and (R)-(S)-((diphenylphosphino) ferrocenyl-ethyldi-t-butylphosphine phosphine ligands can be obtained from Chemi S.p.A. and Solivas, respectively.

Still another embodiment of this invention is when the metal catalyst is iridium, rhodium or ruthenium with the appropriate counterions, preferably ruthenium. Examples of ruthenium catalysts are those derived from $[(arene)RuX_2]_2$+ bisphosphine or (P—P)$RuX_2$. Specific examples of the catalysts are $[(p\text{-cymene})RuCl_2]_2$, $RuCl_2(DMF)_x$, $[Rh(COD)Cl]_2$, $[Rh(NBD)Cl]_2$, [Rh(COD)2]X, $Rh(acac)(CO)_2$, $Rh(ethylene)_2(acac)$, $Rh(CO)_2Cl_2$, $Ru(RCOO)_2$(diphosphine–R=alkyl or aryl), $Ru(methallyl)_2$(diphosphine), $Ru(COD)(methallyl)_2$, $RuCl_2(COD)$, $RuX_2$(diphosphine), $[Ir(COD)Cl]_2$, $[Ir(COD)_2]X$, wherein X=halogen, $BF_4$, $ClO_4$, $SbF_6$, $CF_3SO_3$, $PF_6$. It is preferably that the metal catalyst and ligand are added as a complex. Examples of metal catalyst/ligand complexes are ((R)-(S)-((diphenylphosphino)ferrocenyl-ethyldi-t-butylphosphine)(COD) RhBF4, ((R,R)-Me-BPE)Rh(COD)OTf, ((R)-(S)-((diphenylphosphino)ferrocenyl-ethyldi-t-butylphosphine)RuCl(p-cymene)]Cl, [((−)-TMBTP)RuCl(p-cymene)]Cl, ((S)-(R)-((diphenylphosphino)ferrocenyl-ethyldi-t-butylphosphine) RuCl(p-cymene)]Cl, [((+)-TMBTP)RuCl(p-cymene)]Cl, ((R)-BINAP)Ru(p-cymene)Cl]Cl, [(s)-Tol-BINAP) $RuCl_2{*}Et_3N]_2$, ((S)-BINAP)$RuCl_2$,, and ((R,R)-Me-DuPhos)Rh(COD)$BF_4$. A preferred metal catalyst-ligand complex is ((R)-(S)-((diphenylphosphino)ferrocenyl-ethyldi-t-butylphosphine)RuCl(p-cymene)]Cl. The catalyst can be prepared by contacting a transition metal salt or its complex and a ligand as described above. The catalyst may be prepared in situ or as an isolated compound.

Another embodiment of this invention is when the hydrogenation is optionally conducted in the presence of a base selected from the group consisting of primary amines such as methylamine, secondary amines such as diisopropyl amine, trialkyl amines such as triethylamine, trimethylamine, dicyclohexylmethylamine, tri-n-butylamine, and the like, alkali metal hydrides such as sodium hydride, potassium hydrogen carbonate, $K_2CO_3$, potassium tert-butoxide or the equivalent lithium sodium and cesium salts and the like, using $H_2$, $D_2$ or $T_2$, preferably $H_2$ and solvents such as alcohols (e.g., ethanol, methanol, 2-butanol, isopropanol, trifluoroethanol and the like), THF, ethylacetate, toluene and the like, preferably the alcohols. A sub-embodiment of the process as recited above is where the hydrogenation step is carried out using a mole ratio of metal catalyst to the compound of formula II of about 0.1% to about 5%, preferably about 0.25 to about 1 mole %, at a temperature of about 0° C. to about 60° C., preferably about 25° C. to about 35° C. Still another sub-embodiment of this invention is realized when the metal catalyst-ligand complex is [((R)-(S)-((diphenylphosphino)ferrocenyl-ethyldi-t-butylphosphine)RuCl(p-cymene)]Cl, [((S)-(R)-((diphenylphosphino)ferrocenyl-ethyldi-t-butylphosphine)RuCl(p-cymene)]Cl, [((−)-TMBTP)RuCl(p-cymene)]Cl, or (+)-TMBTP)RuCl(p-cymene)]Cl.

This invention further relates to a process for making a compound of formula IV:

Formula IV

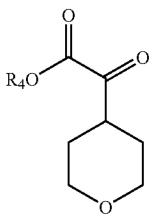

comprising (1) contacting a solution containing a compound of formula VII or salt thereof:

Formula VII

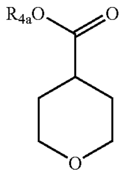

with a strong base;

(2) adding a dialkyloxalate; and (3) adding an acid while maintaining the temperature at about or below 10° C. to produce a compound of formula IV as an ester ($R_4$ is $C_{1-4}$ alkyl), or adding a base to produce the compound of formula IV as an acid ($R_4$ is hydrogen), wherein $R_4$ represents H, $C_{1-4}$ alkyl, and $R_{4a}$ represents H, $C_{1-4}$ alkyl, magnesium, lithium or sodium. Generally, the strong base is added to the solution at a temperature of about −20° C. to about 5° C., preferably 10° C. to about 0° C. Solutions of Formula VII can comprise solvents such as THF, ether and the like. The dialkyloxalate is generally added at a temperature of about −30° C. to about −0° C., preferably about −20° C. to about −5° C. Examples of salts of formula VII are magnesium, lithium, potassium and sodium, wherein $R_{4a}$ is Mg, Li or Na for this particular reaction.

Examples of strong bases are alkyl magnesium halides such as iPrMgCl, PrMgCl, EtMgCl,MeMgCl, LDA, Mg diisopropylamide, and sodium, potassium or lithium hydride and the like. Examples of the dialkyloxalate are dimethyloxalate, diethyloxoate and the like. Examples of acids are TFA, HCl, $H_2SO_4$ and the like. Examples of bases that are added to provide $R_4$=acid are NaOH, LiOH, KOH and the like.

This invention also relates to a process for making a compound of formula III, IIIa or mixture thereof as recited above or a pharmaceutically acceptable salt thereof, comprising (1) asymmetric hydrogenation of the compound of formula IX:

Formula IX

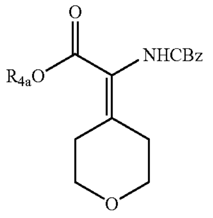

in the presence of a rhodium or ruthenium catalyst/ligand complex to produce a compound of formula IXa, IXb or a mixture thereof;

Formula IXa

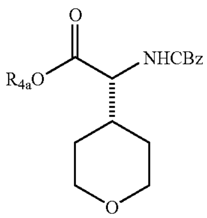

or

-continued

Formula IXb

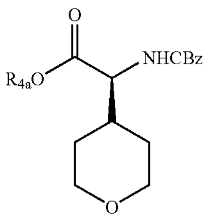

(2) hydrogenolysis of a compound of formula IXa, IXb or a mixture thereof in the presence of a palladium catalyst to produce a compound of formula VIII, VIIIa, a pharmaceutically acceptable salt or mixture thereof, wherein P* is an acid selected from the group consisting of HCl, HI, HBr, acetic acid, TFA, PTSA, and HBF4;

Formula VIII

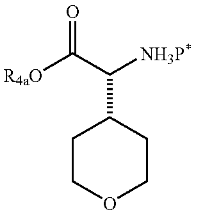

or

Formula VIIIa

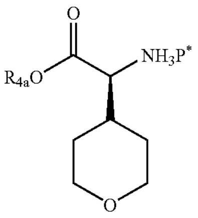

(3) coupling the compound of formula VIII or VIIIa or mixture thereof with compound of formula X:

Formula X

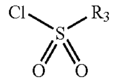

in the presence of a base;

(4) hydrolyzing and purifying the coupled compound to produce a compound of formula III, IIIa or mixture thereof, wherein the base is triethylamine, diisopropylethylamine, tri-n-butylamine, NaOH, LiOH, KOH, $NaHCO_3$, $Na_2CO_3$ and the like, $R^3$ is as described herein and $R^{4a}$ represents H, $C_{1-4}$ alkyl, magnesium, lithium or sodium.

Examples of rhodium or ruthenium catalyst/ligand complex are (+)-1,2-bis(2R,5R)-2,5-dimethylphospholano)ethane(cyclooctadiene)rhodium(I)trifluoromethanesulfonate=Rh(COD)(2R,5R-BPE)OTf; ((R,R)-Me-DuPhos)Rh(COD)

$BF_4$; $(COD)_2RhOTf$/((R)-(S)-((diphenylphosphino)ferrocenyl-ethyldi-t-butylphosphine), and ((R,R)-Me-BPE)Rh (COD)OTf, [((R)-(S)-((diphenylphosphino)ferrocenyl-ethyldi-t-butylphosphine)RuCl(p-cymene)]Cl, [((S)-(R)-((diphenylphosphino)ferrocenyl-ethyldi-t-butylphosphine) RuCl(p-cymene)]Cl, [((+)-TMBTP)RuCl(p-cymene)] Cl and [((−)-TMBTP)RuCl(p-cymene)]Cl. An example of a palladium catalysts is Pd/C.

The hydrogenolysis can be conducted using hydrogen gas or a compound which forms hydrogen. The preferred reaction involves $H_2$ gas with a palladium (Pd/C) catalyst. If necessary, a base can be added. A preferred base is sodium hydroxide or sodium bicarbonate.

Suitable pharmaceutically acceptable salts of the compounds used in this invention include acid addition salts such as hydrochloride, hydrobromide, citrate, maleate and salts formed with phosphoric and sulphuric acid. In another aspect suitable salts are base salts such as an alkali metal salt for example sodium or potassium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. Preferred pharmaceutically acceptable salts are sodium and potassium salts.

In vivo hydrolysable esters are those pharmaceutically acceptable esters that hydrolyze in the human body to produce the parent compound. Such esters can be identified by administering, e.g. intravenously to a test animal, the compound under test and subsequently examining the test animal's body fluids. Suitable in vivo hydrolysable esters for carboxy include C1-6alkoxymethyl esters for example methoxymethyl, C1-6 alkanolyloxymethyl esters for example pivaloyloxymethyl, phthalidyl esters and the additional esters disclosed in U.S. Pat. No. 5,478,820, which is herein incorporated by reference in its entirety.

The following non-limiting examples, given by way of illustration, is demonstrative of the present invention.

Definition of terms are:

HOBT—hydroxybenzotriazole; DMF—dimethylformamide; DMAc—dimethylacetamide; DIEA—diisopropylethylamine; TMSONH2—O-trimethylsilylhydroxylamine; TFA—trifluoroacetic acid; PTSA—toluenesulfonic acid; DCM—dichloromethane; EDC—1-(3-dimethylaminopropyl)-3-ethylcarbodiimide; THF—tetrahydrofuran; DIC—N,N'diisopropylcarbodiimide; DMF—dimethylformamide; DMAP—4-dimethylaminopyridine; NMP—1-methyl-2-pyrrolidinone; EDTA—ethylenediaminetetraacetic acid, sat'd=saturated; h=hour; ppm=parts per million; min=minute; HPLC=high performance liquid chromatography; RT or rt=room temperature; temp=temperature; KF=Karl Fisher; NMR=nuclear magnetic resonance; g=gram; MTBE=tert-butyl methyl ether; TEA=triethylamine; L=liter; PTFE=polytetrafluoroethylene; IPA=isopropyl alcohol; IPAc=isopropylacetate

PREPARATIVE EXAMPLE 1

Synthesis of the 4-Fluoro-3-methylbenzenesulfonamide Intermediate

Alternative Routes:

Direct Chlorosulfonylation

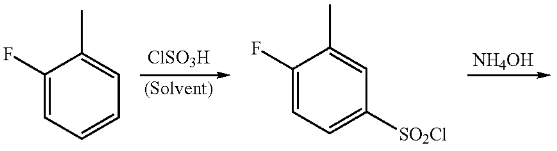

9 2

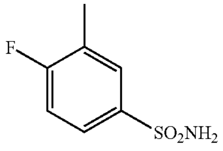

7

Sulfonation/ chlorination

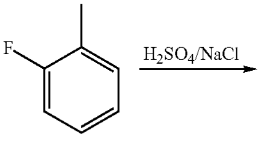

9

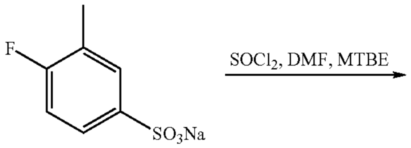

10

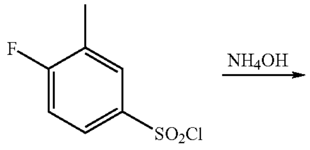

7

2

Diazotization/ Chlorosulfonylation

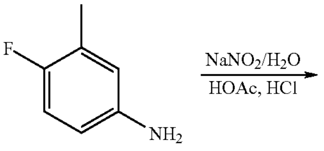

11

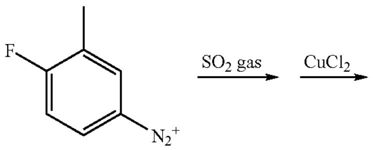

12

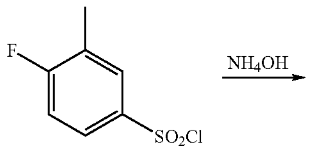

7

2

1. Chlorosulfonylation Route

Preparation of sulfonyl chloride (2)

Mixture of chlorosulfonic acid (40 mL, 600 mmol) and 1,2-dichloroethane (90 mL) was cooled to <2° C. o-Fluorotoluene 9 (22.02 g, 200 mmol) was added slowly over 3 h at <5° C. The resulting solution was warmed to RT and was stirred at RT for 4 h. The solution was cooled to <0° C. Heptane (200 mL) was added, followed by 100 mL of water at <10° C. (HCl gas generated). Aqueous layer was cut. Organic layer was washed with 100 mL of 10% brine. The organic solution was concentrated at 40° C. under 20 mmHg. Crude sulfonyl chloride 2 (39.7 g) was obtained as oil. By HPLC, it was 96.9 A %. (derivatized with piperidine). The oily 2 was dissolved in 40 ml of heptane. The solution was cooled to 18° C. and was seeded. Slurry formed and it was cooled to 4° C. slowly. Filtration afforded some white solid 2. After vacuum drying, 31.55 g solid sulfonyl chloride 2 was obtained. It was 99.0 A % and $96.2^{wt}$ % pure and yield was 73%.

Preparation of sulfonamide (7) from crystalline sulfonyl chloride (2)

Crystalline sulfonyl chloride 2 (31.52 g, $96.2^{wt}$ % pure, 145 mmol, 0.8%) from above procedure was dissolved in 190 mL of MTBE. Ammonium hydroxide solution (28%, 30 mL) and water (30 mL) were added. The mixture was stirred for 1.5 h. 75 mL of 1 M $H_2SO_4$ was added. Aqueous layer was cut. Organic layer was washed with 100 mL of 10% brine. The organic solution was concentrated to 100 mL and 40 mL of heptane was added. The mixture was heated to 48° C. to dissolve all solids. Resulting solution was cooled to 40° C. and was seeded. Slurry formed. 160 mL of heptane was added over 1 h at 40° C. The slurry was cooled to RT over 1 h, then was cooled <5° C. and was aged at <5° C. for 20 min. Filtration afforded some crystalline solid. Cake was rinsed with 50 mL of 1:2 MTBE/heptane. After vacuum oven drying, 27.20 g of sulfonamide 7 was obtained as white crystalline solid. By HPLC it was 99.9 A % and $\sim 100^{wt}$ % (vs. reference) pure and yield was 99%. Mp: 98° C. $^1$H-NMR (400 MHz, $CD_3CN$): δ 2.32 (d, 2.0 Hz, 3H), 5.68 (broad, 2H), 7.20 (t, 9.1 Hz, 1H), 7.70~7.74 (m, 1H), 7.78~7.80 (m, 1H). $^{13}$C-NMR (100 MHz, $CD_3CN$): δ 13.6 (d, 3.9 Hz), 115.4 (d, 24.0 Hz), 125.9 (d, 9.5 Hz), 126.2 (d, 18.4 Hz), 129.6 (d, 6.4 Hz), 139.0 (d, 3.2 Hz), 163.1 (d, 250 Hz). Anal. Calcd for $C_7H_8FNO_2S$: (189.21): C, 44.44; H, 4.26; S, 16.95. Found: C, 44.51; H, 4.05; S, 16.92.

Preparation of sulfonamide (7) without Isolation of sulfonyl chloride (2)

The mixture of chlorosulfonic acid (22 mL, 330 mmol) and 40 mL of 1,2-dichloroethane was cooled to <2° C. o-Fluorotoluene 9 (11.0 g, 100 mmol) was added slowly over 2 h at <5° C. The resulting mixture was warmed to RT and was stirred at RT for 3 h. The mixture was cooled to <0° C. Heptane (100 mL) was added, followed by 50 mL of water at <10° C. Aqueous layer was cut. Organic layer was washed with 50 mL of 20% brine then, 50 mL of 10% $KHCO_3$. The organic solution was concentrated at 40° C. under 20 mmHg. Crude sulfonyl chloride 2 was obtained as greenish color oil. It was 19.68 g. By HPLC, it was 95.7 A % pure. HPLC sample was treated 1 drop of piperidine. The oily 2 was dissolved in 150 mL of MTBE. 17 mL of 28% ammonium hydroxide solution was added. The mixture was stirred for 1 h. Internal temperature increased slowly up to 44° C., then decreased. HPLC showed <0.1% of sulfonyl chloride 2. 25 mL of 1 M HCl was added. Aqueous layer was cut. Organic layer was washed with 50 mL of 10% brine. The organic solution was concentrated to 50 mL. The solution was heated to 45° C. and 20 mL of heptane was charged. The mixture was cooled to 43° C. and was seeded. Slurry formed. 80 mL more of heptane was added over 2 h at 43° C. The slurry was cooled to RT slowly and was aged at RT overnight. The slurry was cooled to 0~5° C. Filtration afforded some solid cake. Cake was rinsed with 30 mL of 1:2 MTBE/heptane. After drying, 16.58 g sulfonamide 7 was obtained. The material was dissolved in 30 mL of MTBE and 6 mL of heptane at 49° C. The solution was cooled to 45° C. and was seeded. A slurry formed and 54 mL more heptane was added over 2 h at 45° C. The mixture was cooled to RT slowly and was aged at RT overnight. The mixture was cooled to <5° C. Filtration and cake rinse with 2:1 heptane/MTBE (20 mL) afforded some solid 7. After vacuum oven drying at 45° C., 15.70 g of sulfonamide 7 was obtained as white solid. By HPLC it was $98.9^{wt}$ % pure. Yield was 79% from 9.

2. Sulfonation-Chlorination Route

Preparation of sulfonate (10)

Concentrated sulfuric acid (1.6 L, 1.45 vol) was added to a flask with 1.10 L (1.10 kg, 1.0 vol, 10 mol) of o-fluorotoluene 9 at RT. The mixture was heated to 80° C. with agitation (temperature control is important due to exothermal reaction). The resulting oil was agitated at 80° C. for 3.5 h until HPLC showed <0.5 A % of 9. The resulting oil was cooled to ~75° C. and 10 L of cold water (9.1 vol) was added quickly. Internal temperature rose up to 96° C. for a moment, then dropped to 48° C. 1.1 L of acetonitrile (1.0 vol) was added, followed by 2.7 kg of solid NaCl. The mixture was heated to 73° C. to dissolve all solids. The clear solution was cooled to 70° C. and was seeded. A slurry formed gradually. The slurry was cooled to RT over ~6 h and was aged at RT for 10 h. It was then cooled to <4° C. over 1.5 h. Filtration afforded some crude salt 10 as pink solids. The solid was washed with 3.3 L of 20% brine (3.0 vol) to give 4.80 kg of wet cake. A portion of the wet solid (3.60 kg, ¾ of total, ¼ of wet cake was saved for other use) was mixed with 7.5 L of 20% brine and 825 ml of acetonitrile. The mixture was heated to 71° C. to dissolve all solids. The solution was cooled to 70° C. and was seeded. A slurry formed gradually. The slurry was cooled to RT over 6 h and was aged at RT for about 10 h. The slurry was cooled to <4° C. over 30 min and was aged at <4° C. for 30 min. Filtration afforded some pinkish color solid. The cake was washed with 2.5 L of 20% brine. The salt 10 was dried in a vacuum oven at 50° C. to give 1.56 kg of solid 10. By HPLC it was 99.8 A % (included regio-isomer) and $83.8^{wt}$ % pure. Yield was 82% after recrystallization. Some product 10 was recrystallized from hot water for analytical purpose. Mp: 370° C. (dec.). $^1$H-NMR (400 MHz, $D_2O$): δ 2.23 (s, 3H), 7.10 (t, 9.2 Hz, 1H), 7.54~7.63 (m, 2H). $^{13}$C-NMR (100 MHz, $D_2O$): δ 13.6 (d, 1.9 Hz), 115.2 (d, 23.4 Hz), 125.0 (d, 9.4 Hz), 126.0 (d, 18.5 Hz), 128.8 (d, 6.1 Hz), 138.0 (d, 3.2 Hz), 162.5 (d, 248 Hz). Anal. Calcd for $C_7H_6FNaO_3S$: (212.17): C, 39.63; H, 2.85; S, 15.11. Found: C, 39.33; H, 2.58; S, 15.20.

Preparation of Solid sulfonyl chloride (2) from sodium sulfonate (10)

Sulfonate 10 ($87.9^{wt}$ % pure, 205.17 g, 850 mmol, 1.0 equiv) was mixed with 1.23 L of MTBE and 20.5 mL of DMF at RT. To the slurry was added 93 mL of $SOCl_2$ (1.5 equiv.). The mixture was heated to 40° C. and was agitated at 40° C.

for 3 h until HPLC showed 0.58 A % of 10. Cold water (615 mL) was added to quench the reaction and dissolve all solids. Aq layer was cut. Organic layer was washed with 2×615 mL of 10% brine. Concentration of organic solution afforded 182 g of oily residue. By HPLC, the residue was chloride 2 (99.8 A % pure) Sample treated with piperidine. The oil was dissolved in heptane (about 182 mL) and total volume was diluted to 260 mL. The solution was cooled to 20° C. and was seeded. A slurry formed and it was cooled slowly to 3° C. over 1 h. The solid was isolated by filtration. After drying under vacuum, 159.12 g of sulfonyl chloride 2 was obtained as off-white solid. It was 99.9 A % and $97.9^{wt}$ % pure. Yield was 88% (75% from o-fluorotoluene 9) and loss in mother liquor was 9.1%. Mp: 37° C. $^1$H-NMR (400 MHz, $CDCl_3$): δ 2.40 (d, 2.0 Hz, 3H), 7.23 (t, 8.7 Hz, 1H), 7.87~7.94 (m, 2H). $^{13}$C-NMR (100 MHz, $CDCl_3$): δ 14.5 (d, 3.2 Hz), 116.4 (d, 24.6 Hz), 127.2 (d, 9.8 Hz), 127.5 (d, 19.2 Hz), 130.7 (d, 6.8 Hz), 139.7 (d, 3.2 Hz), 165.0 (d, 258 Hz). Anal. Calcd for $C_7H_6ClFO_2S$: (208.64): C, 40.30; H, 2.90; S, 15.37. Found: C, 40.41; H, 2.71; S, 15.48.

Preparation of sulfonamide (7) from sulfonate (10) without Isolation of (2)

Sulfonate 10 ($83.8^{wt}$ % pure, 1519 g, 6.00 mol, 1.0 equiv) was mixed with 9.1 L of MTBE and 151 mL of DMF at RT. To the slurry was added 656 ml of $SOCl_2$ (1.5 equiv). The mixture was heated to 40° C. and was agitated at 40° C. for 3 h until HPLC showed 0.30 A % of 10. The mixture was cooled to 35° C. and 4.5 L of cold water were added to quench the reaction. Internal temperature increased to 40° C., and then dropped. The mixture was agitated for 5 min and was settled. The aqueous layer was cut and the organic layer was washed with 2×4.5 L of 10% brine. The organic solution was vacuum distilled at <RT adding 9.0 L of fresh MTBE to maintain constant volume. After this distillation, there was no $SO_2$ in the solution and 1.22 L of 28% ammonium hydroxide solution and 1.22 L of water were added. The mixture was agitated for 1 h. Internal temperature increased slowly up to 38° C., then decreased. HPLC showed <0.1% of sulfonyl chloride 2. $H_2SO_4$ (1 M, 4 L) was added. pH of aqueous layer was 1. The aqueous layer was cut and the organic layer was washed with 4.5 L of 10% $KHCO_3$, then with 4.5 L of 10% brine. The organic solution was concentrated to 3 L. The solution was heated to 45-50° C. and 0.9 L of heptane was charged. The mixture was seeded at 45° C. Slurry formed. 3.6 L more of heptane was added over 1 h at 45° C. The slurry was cooled to 2° C. over 30 min and was aged at 2° C. for 30 min. The product was isolated by filtration. The cake was rinsed with 1 L of 1:1 MTBE/heptane. After vacuum oven drying at 45° C., 1063 g of sulfonamide 7 was obtained as white crystalline solid. By HPLC it was 99.4 A % and about $100^{wt}$ % pure and yield was 94% from sulfonate 10.

3. Diazotization/Chlorosulfonylation Route

Preparation of (7) Via diazonium (12)

4-Fluoro-3-methylaniline 11 (12.52 g, 100 mmol, 1.0 equiv) was dissolved in 20 mL of acetic acid. Water (14 mL) was added. The solution was cooled to 10° C. and 26 mL of conc. HCl was added, which generated a slurry. The slurry was cooled to 4° C. $NaNO_2$ aq (7.04 g in 12 mL of water, 1.02 equiv) was added slowly at <8° C. over 30 min. Brownish color clear solution formed. The solution was kept at <5° C. and was slowly added through a PTFE tube to another flask with mixture of 47 g of $SO_2$, 100 mL of acetic acid, and $CuCl_2$/conc. HCl solution (3.40 g/20 mL) over 2.7 h at RT. After addition, 6 mL of water was used for rinse. The green-yellow color mixture was agitated at RT for another 2 h until HPLC showed no diazonium 12. The mixture was extracted with 3×100 mL of heptane and the combined organic solution was washed with 100 mL of 10% brine. Concentration afforded 19.72 g of 2 as oil. By HPLC, it was 96.8 A % and $94.2^{wt}$ % pure. Yield of 2 was 89%.

Preparation of sulfonamide (7) from sulfonyl chloride (2)

Oily sulfonyl chloride 2 (19.70 g, $94.2^{wt}$ % pure, 88.9 mmol) from the above procedure was dissolved in 125 mL of MTBE. Ammonium hydroxide solution (28%, 16 mL) and water (16 mL) were added. The mixture was stirred for 1.5 h until HPLC showed no 2. $H_2SO_4$ (1 M, 40 mL) was added and aqueous layer was cut. Organic was washed with 50 mL of 10% $KHCO_3$, then with 50 mL of 10% brine. The organic solution was concentrated to 50 mL and the concentrate was heated to 45° C. Heptane (20 mL) was added at 45° C. The solution was seeded and a slurry formed. More heptane (80 mL) was added over 2 h at 45° C. The resulting slurry was cooled to RT over 1 h, then was cooled <5° C. and was aged at <5° C. for 20 min. Filtration afforded some crystalline solid and the cake was rinsed with 30 mL of 1:2 MTBE/heptane. There was 2.8% loss of product 7. After vacuum oven drying, 16.06 g of sulfonamide 7 was obtained as white crystalline solid. By HPLC, the solid was 99.6 A % and ~100 wt % (vs. reference) pure. The yield of 7 was 95% from 2.

Scheme 1

Synthesis of (2R)-2-{[(4-Fluoro-3-methylphenyl)sulfonyl]amino]-N-hydroxy-2-(tetrahydro-2H-pyran-4-yl)acetamide

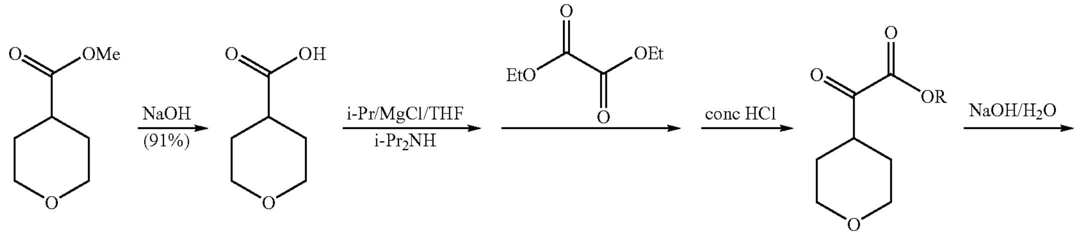

15 16 17a R = Me
17b R = Et

-continued

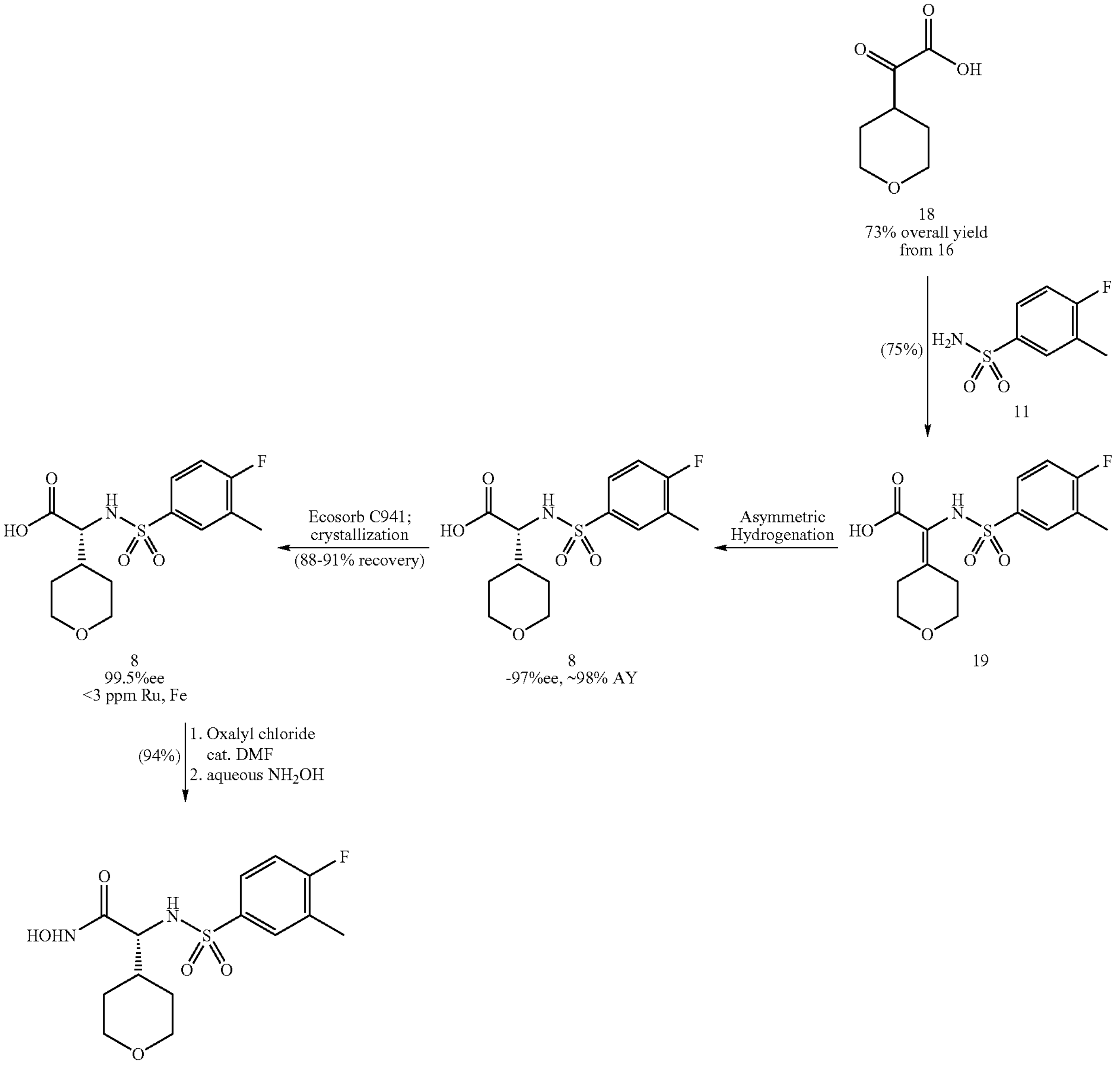

(2R)-2-{[(4-Fluoro-3-methylphenyl)sulfonyl]amino]-N-hydroxy-2-(tetrahydro-2H-pyran-4-yl)acetamide

EXAMPLE 1

From Compound 15 (THP Methyl Ester) to Compound 16 (THP Acid)

THP methyl ester 15 (3.03 kg, 21 mol) was charged to a mechanically-stirred 22 L round bottom flask, followed by water (3.0 L) and this mixture was cooled to 10° C. NaOH (50 wt %, 1.15 L, 1.04 equiv) was then added at a rate such that the internal temperature did not exceed 50° C. Upon completion of the addition, a batch concentrator was used to remove ~1.3 L of solvent. The resulting solution was cooled to 10° C., then concentrated HCl (300 mL) was added, followed by MTBE (3.6 L), and the remainder of the concentrated HCl (1590 mL), keeping the temperature below 20° C. The organic layer was then separated and the aqueous treated with NaCl (525 g). The aqueous layer was then extracted with MTBE (3.6 L), and the combined organics were filtered to remove residual NaCl then stripped to ~½ the original volume. n-Heptane (1.8 L) was added, followed by batch concentration to remove residual MTBE. More n-heptane (1.8 L) was added with vigorous stirring. The resulting thick white solid precipitate was then filtered and dried under $N_2$ for 1 h, then at 40° C. under vacuum for 64 h to give 2.47 kg (91% yield) of THP Acid 16.

HPLC Assay

Column: Zorbax RX-C8, 4.6 mm×250 mm

Solvents: 0 to 3 min: 35% ACN, 65% $KH_2PO_4/K_2HPO_4$ Buffer; 3 to 5 min: 60% ACN, 40% $KH_2PO_4/K_2HPO_4$ Buffer; 5 to 7 min: 35% ACN, 65% $KH_2PO_4/K_2HPO_4$ Buffer; Flow: 1.0 mL/min; Sample volume: 5 μL; Wavelength: 210 nm; Retention times: THP Ester 15: 4.6 min; THP Acid 16: 2.1 min.

EXAMPLE 2

From Compound 16 (THP acid) to Compound 17b (THP α-Ketoester)

THP Acid 16 (1.0 kg, 7.7 mol) was added to a 22 L round bottom flask with mechanical stirrer and thermocouple, attached to a batch-concentrator. THF (3.0 L) was added to dissolve 16 then the solvent was stripped to 1 L. THF (2.0 L) was added, and the solvent was again stripped to 1 L. A Karl Fisher (KF) of the mixture was <500 ppm. An addition-funnel was then added, and the mixture was cooled to ~−30° C. iPrMgCl (2M in THF, 8.1 L, 16.2 mol) was then added over 1 h, maintaining the temperature between −10° C. and 0° C. Diisopropylamine (1.19 L, 8.5 mol) was then added all at once. This dark solution was then warmed to 35° C. and stirred at this temperature for 30 min. Vigorous evolution of propane gas was observed. The initial 35° C. temperature plateau is designed to complete formation of the magnesium diisopropylamide, without Grignard addition to the carboxylate.

The reaction mixture was then was warmed to 55° C. and stirred for 2 h. An off-white slurry formed after ~30 min at 55° C. This mixture was then cooled to −20° C., and diethyl oxalate (1.15 L, 8.5 mol) was added over 25 min keeping the temperature below −5° C. After warming to RT over 90 min, the mixture was stirred for 1 h and stored overnight at 3° C. Aging this solution at RT for 20 h does not result in any significant loss in yield.

The resulting solution was cooled to 0° C., then EtOH (500 mL) was added over 15 min, forming a light yellow precipitate and giving a slight exotherm. This mixture was cooled to −10° C., then HCl (concentrated, 2.03 L) was added carefully over 1 h, so that the internal temperature did not exceed 10° C., with evolution of $CO_2$. The mixture grew thick upon acid addition, but was easy to stir. Off-gassing of $CO_2$ should be carefully controlled by the rate of HCl addition so that the batch does not bump.

This mixture was warmed to 50° C. for 45 min, then cooled to RT and diluted with water (2.0 L) and MTBE (1.0 L). All of the solids immediately dissolved. The aqueous layer was then cut, and the organics were diluted with MTBE (3.0 L), and the resultant was washed successively with 1.0 N HCl (2.0 L) and brine (20% sat'd., 2.0 L). HPLC assay yield analysis of 3 using the protocol described below showed:

HPLC assay yield of α-ketoester 17b.

| | g product | % product |
|---|---|---|
| Final Organics | 1066 | 74.5 |
| Aqueous cut 1 | 77 | 5.4 |
| Aqueous cut 2 | 66 | 4.6 |
| Aqueous cut 3 | 11 | 0.8 |
| Total: | 1220 | 85.3 |

HPLC Assay

Due to poor HPLC peak shape of the α-ketoester 17b, an analysis was developed using the 2,4-dinitrophenylhydrazine derivative 22, which showed improved peak shape and UV response. A reference standard of the hydrazone was prepared by mixing 2,4-dinitrophenylhydrazine (2.50 g, ~70% pure, 8.8 mmol) and chromatography-purified ester 17b (1.87 g, 10 mmol) in MeOH at RT for 2 h, followed by filtration of the precipitate product and recrystallization from hot MeOH to afford 1.94 g of high purity material.

22

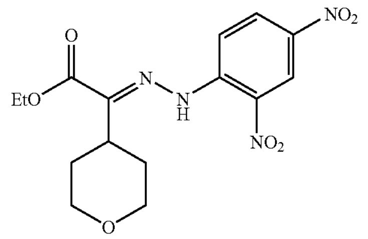

The reaction assay was run as follows: 2,4-dinitrophenylhydrazine (11.32 g) was dissolved in acetonitrile (800 mL). A sample containing approximately 20 mg of α-ketoester 17b was dissolved in 3 mL of the hydrazine solution, and then 50 μL of conc. $H_2SO_4$ was added. This was aged for 1 h at RT, then diluted to 50 mL in a volumetric flask with acetonitrile for HPLC analysis. This assay agreed well with a $^1$H-NMR assay for the α-ketoester 17b that was developed using mesitylene as an internal standard.

HPLC Assay

Column: Zorbax RX-C8, 4.6 mm×250 mm; Solvents: 50% $CH_3CN$, 50% 0.25% $HClO_4$; Flow: 1.0 mL/min; Temperature: 25° C.; Sample volume: 5 1 μL; Wavelength: 210 nm (Ref 300, 100); Retention times: Dinitrophenylhydrazine: 3.3 min; Hydrazone adduct 22: 6.6 min.

EXAMPLE 3

From Compound 17b (THP α-ketoester) to Compound 18 (THP α-Ketoacid)

The organic solution containing THP α-ketoester 17b (1.07 kg, 5.79 mol) was added to a solution containing water (3.5 L), KOH (89%, 486 g, 7.70 mol) and $K_2HPO_4$ (435 g, 2.50 mol). Use of a buffered hydrolysis system minimizes side-products. This was stirred at RT for 2 h, then the organic layer was cut. The aqueous layer was then concentrated to remove EtOH. To the resulting solution was added a 3:1 MTBE/THF mixture (5.0 L) and this solution was cooled to 10° C. Concentrated HCl (1.0 L) was added, followed by NaCl (500 g). The organic layer was collected, then the aqueous layer was washed with 3:1 MTBE/THF (2×5.0 L). The resulting combined organics was stripped to a thick residue, then was flushed with MTBE (4.0 L). The resulting solution was filtered through an in-line filter, then concentrated to 1.7 L and heated to 49° C. to dissolve all solids. The solution was cooled to 45° C., then seed was added. Upon cooling to 40° C., a slurry formed. n-Heptane (5.1 L) was then added over 2 h at 40° C. The mixture was then cooled to 5° C. over 50 min and filtered rinsing the solids with n-heptane (1.0 L). After drying at 50° C. in a vacuum oven, 891.4 g (95.3% yield from 17b) of off-white solid was obtained (99.3 A %, 97.9 wt %). The overall yield of 18 from 16 was 71.7%.

HPLC Assay

Column: Zorbax RX-C8, 4.6 mm×250 mm; Solvents: 50% $CH_3CN$, 50% 0.25% $HClO_4$; Flow: 1.0 mL/min; Temperature: 25° C.; Sample volume: 5 μL; Wavelength: 210 nm (Ref 360, 100); Retention times: α-Ketoacid 18: 2.7 min; α-Ketoester 17b: (broad) 4.7 min.

EXAMPLE 4

Sulfonenamide acid

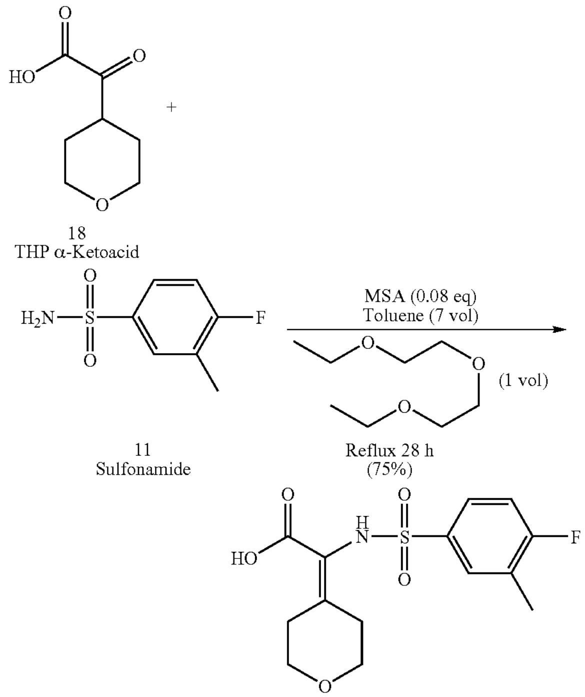

18
THP α-Ketoacid

11
Sulfonamide

19
Sulfonenamide acid

α-Ketoacid 18 (185.0 g, 1.17 mol) was mixed with sulfonamide 11 (201.3 g, 1.06 mol) in a 5 L round bottom flask with a mechanical stirrer, a thermocouple and a Dean-Stark trap. Diethylene glycol diethyl ether (185 mL) and toluene (1.3 L) were added, followed by methanesulfonic acid (5.5 mL, 85 mmol). Diethylene glycol diethyl ether is a high-boiling solvent added to keep the product, which is very insoluble in toluene, in solution throughout the reaction. This mixture was heated to reflux (116-117° C.) for 28 h, monitored by LC analysis. Some toluene was lost during the reaction. To the dark solution was then added toluene (2.6 L) keeping the temperature above 110° C. Near the end of toluene addition, a seed bed formed. This mixture was cooled slowly to 5° C. over 3 h, was aged at this temperature for 1 h. The solids were isolated by filtration rinsing with toluene (2×1.3 L). If conversion is lower than expected, additional toluene washes can be used to remove unreacted starting materials from the solids with minimal loss of product.

The resulting solid was dried under air for 64 h, giving 281 g of 19. Mother liquor and rinse losses were 12.3 g (3.5%) of product 19 and 19.8 g of unreacted sulfonamide (9.8%). The solids (275 g) were then dissolved in MeOH (825 mL) at 50° C., then water (1.0 L) was added over 30 min until a seed-bed formed. After aging 30 min, more water (925 mL) was added, and the mixture was cooled to RT. The solids were filtered and washed with water (1.0 L), then dried overnight under air giving 280 g of material as the hydrate (93.4 wt %, KF=52200 ppm). Mother liquor and rinse losses were 6.1 g (2.2%). This material (278 g) was dried by dissolving in EtOH (3.0 L, KF ~300 μg/mL), and flushing the solution with dry EtOH (4.0 L, KF ~50 μg/mL) until the KF of the solution was ~600 μg/mL. The final solution was in ~1840 mL EtOH (~16.5 wt %). LC assay showed 256 g (73% yield) of 19 in the solution. Including the solid samples removed gives a yield of 75%.

HPLC Assay

Column: Zorbax RX-C8, 4.6 mm×250 mm; Solvents: 0 to 3 min: 35% ACN, 65% $KH_2PO_4/K_2HPO_4$ Buffer; 3 to 5 min: 60% ACN, 40% $KH_2PO_4/K_2HPO_4$ Buffer; 5 to 7 Min: 35% ACN, 65% $KH_2PO_4/K_2HPO_4$ Buffer; Flow: 1.0 mL/min; Sample volume: 5 μL; Wavelength: 210 nm Retention times: α-ketoacid 18: 1.9 min; Sulfonenamide acid 19: 2.2 min; Sulfonamide 11: 5.8 min.

EXAMPLE 5

From Compound 19 (sulfonenamide acid) to Compound 8 ((R)-Sulfonamide acid)

Catalyst Preparation.

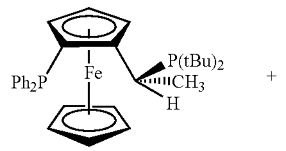

(R,S)-$^t$Bu-Josiphos = ((R)-1-[(S)-2-(Diphenylphosphino)ferrocenyl]ethyldi-t-butylphoshine 0.5 $[(p\text{-cymene})RuCl_2]_2$ —50° C., EtOH/DCE→ $[((R,S)\text{-}^t\text{Bu-Josiphos})RuCl(p\text{-cymene})]Cl$ In a nitrogen-filled glovebox (<10 ppm $O_2$)[(p-cymene) $RuCl_2]_2$ (1.16 g, 1.90 mmol) and (R)-(S)-((diphenylphosphino)ferrocenyl-ethyldi-t-butylphosphine (2.11 g, 3.90 mmol, 2.05 equiv) were combined in a 1 L round bottom flask. To the solids were added nitrogen degassed ethanol (234 mL) and DCE (130 mL). If DCE is added first then the resulting solution will be immediately homogeneous, although the order of addition does not affect the outcome of the reaction. Solution will be dark red/brown at this time. The flask was septum sealed and brought outside the glovebox where it was placed in a heating mantle. A gentle nitrogen sweep was applied and a thermocouple was inserted into the solution. Gentle heating was applied until T=50° C. and then was kept at 50° C. for 1 h. Once the reaction temperature has been reached the solution will darken until it is opaque in appearance. After 1 h, beating was discontinued and the solution was allowed to cool to RT. The flask was then taken again into a nitrogen-filled glovebox.

Hydrogenation

In a nitrogen filled glovebox (<10 ppm $O_2$), the solution of [((R)-(S)-((diphenylphosphino)ferrocenyl-ethyldi-t-butylphosphine)RuCl(p-cymene)]Cl (340 mL, 3.56 mmol, 0.54 mol %, substrate/catalyst=187) was transferred to a 0.5 L stainless steel vessel (see figure below). Ethanol (100 mL) was charged to a 0.15 L stainless steel vessel. These two vessels were connected with a ball-valve separating the two vessels.

To the ethanol solution of 19 was added TEA (34.4 g, 340 mmol, 0.51 equiv). Prior to addition of TEA, water content of the ethanol solution of 19 was determined to be approximately 1000 ppm. Higher water content has been observed to negatively impact the selectivity of the hydrogenation. This solution was drawn into a 1 gallon stirred autoclave via vacuum followed by an ethanol (300 mL) rinse. The solution was then degassed with nitrogen (3×). The stainless steel vessels containing the catalyst solution were connected to the autoclave via flexible tubing. The autoclave was placed under partial vacuum and the catalyst solution was drawn into the autoclave followed by the EtOH rinse. The solution was degassed with $H_2$ (500 psig) 3× with stirring. The reaction temperature was increased to 30° C. The reaction progress was monitored by hydrogen uptake from a reservoir. Uptake was very rapid for the first 1.5 h with no uptake being observed after 3 h. End of reaction was determined by HPLC analysis. Upon completion, the hydrogen was vented and the reaction was drained into a polyjug. The vessel was rinsed with EtOH (1 L). The HPLC assay yield was determined to be 97.2% and the ee was 96.9%.

HPLC Assay

Column: Chiralpak AD-H, 25 cm×4.6 mm; Solvents: 90/10 heptane/IPA (0.4% triethylamine, 0.4% trifluoroacetic acid); Flow: 1.0 mL/min, 40° C.; Sample volume: 5 μL; Wavelength: 224 nm;

Retention times: (S)-Sulfonamide acid 8: 16.95 min; (R)-Sulfonamide acid 8: 21.54 min Sulfonenamide acid 19: 23.09 min.

Cymene catalyst preparation is known in the art. Illustrations for the process are disclosed in Mashina, K. et al., Journal of the Chemical Society, Chemical Comm. 1989, vol. 17 page 1208-1210 and Takaya, H. et al., Pure and Applied Chemistry 1990, vol 62, Issue 6, page 1135-1138.

EXAMPLE 6

Ru Reduction/% ee Upgrade

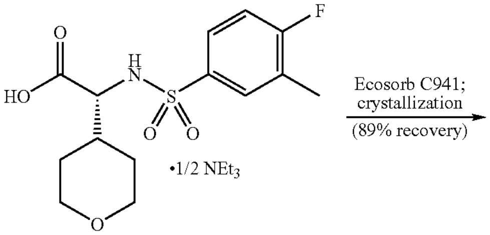

8
97% ee
Sulfonamide Acid

-continued

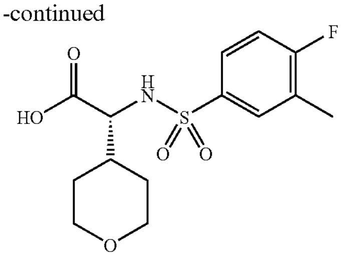

8
99.5% ee
<3 ppm Ru, Fe
Sulfonamide Acid

Sulfonamide acid 8 (436 g, 1.32 mol, in EtOH) was concentrated to ~1 L vol by rotary evaporation (50° C. bath, 29 in Hg) and evaporated at constant volume adding 2.3 L of IPAc. The dark solution was diluted to 2.6 L vol with more IPAc and transferred to an extractor with a 1 L IPAc rinse. 1N HCl (680 ml} was added (to pH 1.3) to neutralize the hemi-triethylamine salt. The aqueous layer was cut (0.4% prod loss) and the organic layer was washed with 960 mL of water (pH 3, 0.7% prod loss). The IPAc solution was agitated with 925 mL of 1.5 N KOH to adjust the pH to 10.4. The clear aqueous layer was collected and the rag layer was filtered through Solka floc pad, rinsing with 200 mL of water. The combined aqueous layer was stirred 30 min with 220 g of Ecosorb C-941 and was filtered through a medium frit sintered glass funnel. The resin was slurry rinsed with 3× water (1.2 L total). The basic solution ~2.5 L) was mixed with 2.2 L of methanol (exothermed from 18° C. to 26° C.) and 1:1 conc $HCl/H_2O$ (210 mL) was added, followed by 40 mL of conc HCl to adjust the pH to 1. The mixture was heated to 40° C. After seeding, no slurry formed, so more water (400 mL) was added at 40° C. over 5 min. The solution was seeded again and a slurry gradually formed. More water (2.4 L) was added at 40° C. over 2 h. The mixture was allowed to cool slowly to RT and age overnight. The resulting slurry was cooled to 4° C., aged for 30 min and filtered, rinsing with 3:1 $H_2O$/MeOH (400 mL). The white solids were dried 2 d in a 50° C. vacuum oven to afford 398 g (98 wt %, >99 A %, 1.3 wt % water) with 89% recovery of 8. Heavy metals were <3 ppm Ru and <3 ppm Fe and optical purity was 99.5% ee.

EXAMPLE 7-16

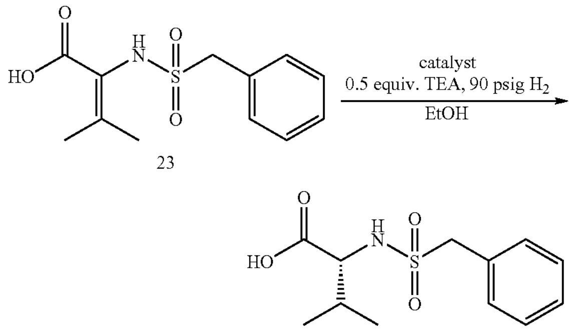

23

(R)-24

| | | | |
|---|---|---|---|
| 23 | 269.32 g/mol | 50.0 mg | 0.186 mmol |
| Triethylamine (TEA) (d = 0.726) | 101.19 g/mol | 9.4 mg | 0.093 mmol |
| Ethanol | | 0.32 mL | |
| [(((-)-TMBTP)RuCl(p-cymene)]Cl (10.4 mM in 1.8:1 EtOH/DCE) | | 0.18 mL | $1.86x10^{-3}$ mmol |

In an nitrogen filled glovebox (<10 ppm $O_2$), tosyl-valine substrate 23 was combined with anhydrous ethanol (0.32 mL) and TEA (9.4 mg, 0.093 mmol) in an 8 mL septum-capped vial fitted with a vent needle. The solution was agitated until homogeneous. Once homogeneous, the catalyst solution was added (0.18 mL, $1.86\times10^{-3}$ mmol). The vial was placed in a glass Fisher Porter hydrogenation bottle. The bottle was pressurized with $H_2$ gas (90 psig) and vented 3 times to degas and finally pressurized again to 90 psig $H_2$. The reaction was agitated for 17 hours at ambient temperature. The Fisher Porter was depressurized and the reaction was sampled for HPLC analysis. Assay yield was determined to be >99% and enantiomeric excess (ee) was determined to be 97.3% ee giving preferentially the (R)-enantiomer of 24.

The following table of substrates were hydrogenated in a manner similar to that described for 23.

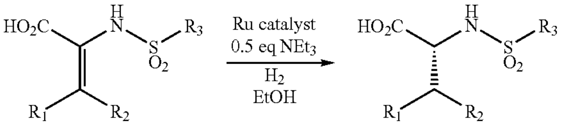

| Entry | ID | scale (mg) | $R_1$ | $R_2$ | $R_3$ | ligand | mol % Ru | T(C) | Time(h) | ee | assay yield[1,2] | config |
|---|---|---|---|---|---|---|---|---|---|---|---|---|
| 1 | 25 | 150.9 | Me | Me | 4-Me-C6H4 | (-)-TMBTP | 1.0% | 25 | 24 | 97.0% | >99% | D |
| 2 | 26 | 150.4 | Me | Me | 4-OMe-C6H4 | (-)-TMBTP | 1.0% | 25 | 24 | 97.6% | 93% | D |
| 3 | 27 | 150.7 | Me | Me | 4-F-C6H4 | (-)-TMBTP | 1.0% | 25 | 24 | 97.2% | 95% | D |
| 4 | 28 | 150.0 | Me | Me | C6H5-CH2 | (-)-TMBTP | 1.0% | 25 | 24 | 97.3% | >99% | D |
| 5 | 29 | 150.6 | Me | Me | C6H5-(CH2)3 | (-)-TMBTP | 1.0% | 25 | 24 | 98.1% | 98% | D |
| 6 | 30 | 150.9 | —(CH2)5— | | 4-Me-C6H4 | (R,S)-tBu-Josiphos[3] | 2.0% | 25 | 24 | 95.9% | >99 | D |
| 7 | 31 | 150.0 | —(CH2)5— | | 4-F-C6H4 | (R,S)-tBu-Josiphos[3] | 1.1% | 25 | 24 | 95.9% | 98% | D |
| 8 | 32 | 150.1 | Me | H | 4-Me-C6H4 | (S,S,S,S)-Me-f-Katalphos | 1.0% | 25 | 24 | 91.4% | 95% | L |
| 9 | 33 | 100.0 | iPr | H | 4-Me-C6H4 | (S,S,S,S)-Me-f-Ketalphos | 5.0% | 40 | 24 | 89.6% | >99% | L |

[1]All reactions were determined to be >99% conversion.
[2]Assay yields were determined using HPLC and comparison to authentic standards.
[3](R,S)-tBu-Josiphos = (R-(S)-((diphenylphosphino)ferrocenyl-ethyldi-t-butylphosphine

| HPLC Information | | | | |
|---|---|---|---|---|
| | | Retention Times (min) | | |
| ID | Assay | starting material | L-product | D-product |
| 25 | A | 21.7 | 18.9 | 45.1 |
| 26 | A | 20.4 | 13.4 | 85.7 |
| 27 | A | 37.2 | 20.8 | 61.0 |
| 23 | A | 22.3 | 16.5 | 26.6 |
| 29 | A | 24.1 | 16.3 | 19.8 |
| 30 | A | 30.8 | 22.1 | 27.8 |
| 31 | A | 35.6 | 23.6 | 39.4 |
| 32 | B | 34.8 | 38.1 | 59.3 |
| 33 | C | 67.9 | 56.2 | 63.7 |

HPLC Assays: (All HPLC analyses were preformed using a Chiralpak AD-H Guard column (10 mm x 4.0 mm, 5 μm) coupled in line with stated column)
A: Chiralpak AD-H, 25 cm x 4.6 mm, 5 μm, at 40° C., 90/10 heptane/IPA (0.4% triethylamine, 0.4% trifluoroacetic acid), flow rate - 1.0 mL/min, detection = 224 nm
B: Chiralpak AD-H, 25 cm x 4.6 mm, 5 μm + Astec Chirobiotic V 10 cm x 4.6 mm, at 40° C., 90/10 heptane/IPA (0.4% triethylamine, 0.4% trifluoroacetic acid), flow rate - 1.0 mL/min, detection = 224 nm
C: Chiralpak AD-H, 25 cm x 4.6 mm, 5 μm, at 40° C., 95/4/1 heptane/IPA (0.4% triethylamine, 0.4% trifluoroacetic acid)/EtOH, flow rate - 1.0 mL/min, detection = 224 nm

Synthesis of N-sulfonyl-α-dehydroamino acids

EXAMPLE 8

25. N-toluenesulfonyl-α-dehydrovaline

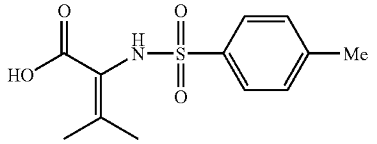

To Ethyl 3-methyl-2-oxobutanoate, (15.0 g, 104.0 mmol) in THF (150 mL) was added $LiOH.H_2O$(5.30 g, 125.0 mmol). This stirred at rt overnight, then the solvent was stripped. The resulting white solid was slurried in MTBE (150 mL) and cooled to 0 C., then HCl (12.1 N, 11.0 mL) was added. The resulting biphasic was warmed to rt, then saturated with $Na_2SO_4$. The inorganic solids were filtered and washed with MTBE (50 mL). The combined organics were stripped to give a light yellow oil. This oil was dissolved in toluene (84 mL) and diethyleneglycol diethyl ether (12 mL) and p-toluenesulfonamide (14.2 g, 83.2 mmol) then methanesulfonic acid (0.54 mL, 8.3 mmol) were added. The resulting mixture was heated at reflux with Dean-Stark removal of water for 24 h, then cooled to rt. The resulting mixture was mixed with EtOAc (45 mL) and $NaHCO_3$ (14.1 g) in water (150 mL). Upon complete $CO_2$ evolution and dissolution, the aqueous layer was separated, then the organics were washed with $NaHCO_3$ (1.6 g) in water (45 mL). The combined aqueous layers were washed with EtOAc (2×45 mL), then cooled to 0 C, and treated with HCl (12.1N, 15.4 mL), to give a white solid precipitate, which upon filtration and drying gave 15.0 g of crude material. This material was dissolved in MeOH (45 mL), then toluene (100 mL) was added. This was heated to 90 C, and the MeOH was removed. Then n-heptane (100 mL) was added slowly over 2 h at 80 C, then cooled slowly to 0 C. Filtration gave 12.0 g of pure white material (54% yield).

mp 188.5-189.5° C. $^1$H-NMR (400 MHz, $CD_3OD$), d 7.67 (d, 2H, 20.1 Hz), 7.32 (d, 2H, 20.1 Hz), 2.42 (s, 3H), 2.09 (s,

3H), 1.79 (s, 3H); $^{13}$C NMR (100 MHz, DMSO-d6), 166.8, 146.9, 142.8, 138.6, 129.6, 126.9, 122.1, 22.1, 21.4, 21.3 ppm. HRMS calcd for C12H14NO4S: (M-H): 268.0644, Found: 268.0638.

EXAMPLE 9

26. N-(4-methoxy)benzenesulfonyl-α-dehydrovaline

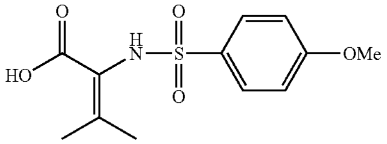

3-methyl-2-oxobutyic acid, sodium salt (2.0 g, 14.2 mmol) was slurried in MTBE (10 mL) and cooled to 0 C, then HCl (12.1 N, 1.3 mL) was added. The resulting biphasic was warmed to rt, then saturated with $Na_2SO_4$. The inorganic solids were filtered and washed with MTBE (10 mL). The combined organics were stripped to give a light-yellow oil. This oil was dissolved in toluene (14 mL) and diethyleneglycol diethyl ether (2 mL) and p-methoxybenzenesulfonamide (2.2 g, 11.6 mmol) then methanesulfonic acid (0.08 mL, 1.2 mmol) were added. The resulting mixture was heated at reflux (65 C) at reduced pressure with Dean-Stark removal of water for 16 h. The resulting mixture was mixed with EtOAc (25 mL) and $NaHCO_3$ (2.0 g) in water (40 mL). Upon complete $CO_2$ evolution and dissolution, the aqueous layer was separated, then the organics were washed with $NaHCO_3$ (0.2 g) in water (11 mL). The combined aqueous layers were washed with EtOAc (11 mL), then cooled to 0 C, and treated with HCl (12.1N, 2.1 mL), to give a white solid precipitate, which upon filtration and drying gave 0.45 g of crude material. This material was passed though silica-gel, eluting with EtOAc to give 0.44 g of pure white product (13% yield).

mp 162.5-163.5° C. $^1$H-NMR (400 MHz, $CD_3OD$), d 7.72 (d, 2H, 22.2 Hz), 7.02 (d, 2H, 22.7 Hz), 3.86 (s, 3H), 2.09 (s, 3H), 1.81 (s, 3H); $^{13}$C NMR (100 MHz, $CD_3OD$), 167.0, 163.2, 150.7, 132.0, 129.2, 121.2, 113.7, 54.9, 21.9, 20.5 ppm. HRMS calcd for C12H14NO5S: (M-H): 284.0593, Found: 284.0591.

EXAMPLE 10

27. N-(4-fluorobenzene)sulfonyl-α-dehydrovaline

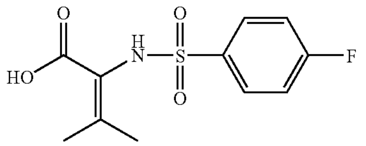

3-methyl-2-oxobutyic acid, sodium salt (5.0 g, 36.2 mmol) was slurried in MTBE (25 mL) and cooled to 0 C, then HCl (12.1 N, 3.1 mL) was added. The resulting biphasic was warmed to rt, then saturated with $Na_2SO_4$. The inorganic solids were filtered and washed with MTBE (25 mL). The combined organics were stripped to give a light-yellow oil. This oil was dissolved in toluene (35 mL) and diethyleneglycol diethyl ether (5 mL) and p-toluenesulfonamide (5.1 g, 29.0 mmol) then methanesulfonic acid (0.19 mL, 2.9 mmol) were added. The resulting mixture was heated at reflux with Dean-Stark removal of water for 24 h, then cooled to 5 C. The resulting solid was filtered, and dried to give 5.4 g of crude material, which was recrystallized from MeOH/water (16 mL/38 mL) to give 4.90 g of pure white solid (62% isolated yield).

mp 172-173° C. $^1$H-NMR (400 MHz, $CD_3OD$), d 7.83-7.86 (m, 2H), 7.22-7.27 (m, 2H), 2.12 (s, 3H), 1.87 (s, 3H); $^{13}$C NMR (100 MHz, $CD_3OD$), 166.6, 166.3, 163.7, 151.6, 136.7 (2 peaks), 129.9, 129.8, 120.8, 115.5, 115.3, 22.0, 20.4 ppm. HRMS calcd for C11H11FNO4S: (M-H): 272.0393, Found: 272.0398.

EXAMPLE 11

28. N-(benzyl)sulfonyl-α-dehydrovaline

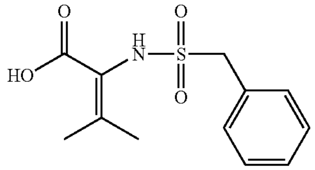

3-methyl-2-oxobutyic acid, sodium salt (5.0 g, 36.2 mmol) was slurried in MTBE (25 mL) and cooled to 0 C, then HCl (12.1 N, 3.1 mL) was added. The resulting biphasic was warmed to rt, then saturated with $Na_2SO_4$. The inorganic solids were filtered and washed with MTBE (25 mL). The combined organics were stripped to give a light-yellow oil. This oil was dissolved in toluene (35 mL) and diethyleneglycol diethyl ether (5 mL) and alpha-toluenesulfonamide (4.90 g, 29.0 mmol) then methanesulfonic acid (0.19 mL, 2.9 mmol) were added. The resulting mixture was heated at reflux with Dean-Stark removal of water for 24 h, then cooled to 5 C. The resulting solid was dissolved in EtOAc (25 mL) and $NaHCO_3$ (4.8 g) in water (50 mL), then the aqueous was cut and the organics were washed with $NaHCO_3$ (0.50 g) in water (20 mL). The aqueous layer was then treated with concentrated HCl (5.2 mL, conc.) at 0 C, to give a solid which was recrystallized from toluene/heptane to give 4.0 g (51% yield) of white solid.

mp 194-195° C. $^1$H-NMR (400 MHz, $CD_3OD$), d 7.45-7.47 (m, 2H), 7.33-7.37 (m, 3H), 4.43 (s, 2H), 2.21 (s, 3H), 2.02 (s, 3H); $^{13}$C NMR (100 MHz, $CD_3OD$), 167.2, 151.4, 130.7, 129.7, 128.0, 127.8, 121.3, 59.0, 22.5, 20.6 ppm. HRMS calcd for C12H14NO4S: (M-H): 268.0644, Found: 268.0644.

EXAMPLE 12

29. N-(propyl-3-phenyl)sulfonyl-α-dehydrovaline

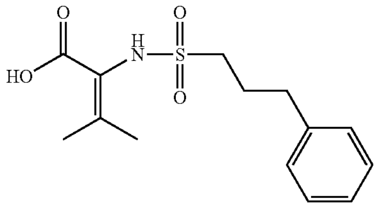

3-methyl-2-oxobutyic acid, sodium salt (2.6 g, 18.8 mmol) was slurried in MTBE (20 mL) and cooled to 0 C, then HCl (12.1 N, 1.6 mL) was added. The resulting biphasic was warmed to rt, then saturated with $Na_2SO_4$. The inorganic solids were filtered and washed with MTBE (20 mL). The combined organics were stripped to give a light-yellow oil. This oil was dissolved in toluene (20 mL) and diethyleneglycol diethyl ether (3 mL) and 3-phenylpropane-1-sulfonamide (3.0 g, 15.1 mmol) then methanesulfonic acid (0.10 mL, 1.5 mmol) were added. The resulting mixture was heated at reflux with Dean-Stark removal of water for 18 h, then cooled to rt. EtOAc (25 mL) and $NaHCO_3$ (2.5 g) in water (50 mL) were added, and this was stirred until all materials dissolved. The aqueous was separated, then the organics were washed with $NaHCO_3$ (0.40 g) in water (10 mL). The combined aqueous layers were then washed with EtOAc (20 mL). The aqueous layer was cooled to 0 C, then HCl (12.1 N, 2.8 mL) was added. The resulting oil was extracted into EtOAc (2×50 mL), while still cold. The organics were passed through a plug of silica-gel, then stripped and the resulting solids recrystallized from toluene (30 mL) to give pure material 2.87 g (67%).

mp 104.5-106° C. $^1$H-NMR (400 MHz, $CDCl_3$), d 7.27-7.31 (m, 2H), 7.16-7.23 (m, 3H), 5.84 (s, 1H), 3.07-3.11 (m, 2H), 3.74 (t, 2H, 18.8 Hz), 2.30 (s, 3H), 2.17-2.24 (m, 2H), 2.16 (s, 3H); $^{13}$C NMR (100 MHz, $CDCl_3$), 170.2, 159.6, 140.2, 128.5, 128.3, 126.3, 119.5, 52.8, 34.2, 25.1, 25.0, 22.6 ppm. HRMS calcd for C14H18NO4S: (M-H): 296.0957, Found: 296.0951.

EXAMPLE 13

30. N-toluenesulfonyl-α-dehydrocyclohexylglycine

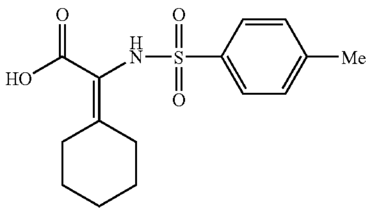

2-cyclohexyl-2-oxoethanoic acid (3.0 g, 19.2 mmol) was combined with p-toluenesulfonamide (2.63 g, 15.4 mmol) in toluene (21 mL) and diethyleneglycol diethyl ether (3 mL). MSA (0.10 mL, 1.5 mmol) was added, and this mixture was heated at reflux for 24 h, then cooled to rt. The resulting solids were mixed with EtOAc (35 mL) and $NaHCO_3$ (2.6 g) in water (60 mL), until all materials dissolved. The aqueous was separated, and the organics were washed with $NaHCO_3$ (0.40 g) in water (10 mL). The combined aqueous layer was then washed with EtOAc (20 mL). The aqueous layer was cooled to 0° C., then treated with HCl (12.1 N, 3.1 mL). The resulting solids were filtered and washed with water and dried to give 4.45 g of crude material. The solids were then recrystallized from EtOAc/MeOH/n-heptane (40 mL/15 mL/70 mL) to give 4.1 g of pure white solid (86% yield).

mp 221-222° C. $^1$H-NMR (400 MHz, $CDCl_3$), d 7.69 (d, 2H, 20.8 Hz), 7.33 (d, 2H, 20.0 Hz), 2.58-2.61 (m, 2H), 2.41 (s, 3H), 2.13-2.16 (m, 2H), 1.48-1.60 (m, 4H), 1.32-1.38 (m, 2H); $^{13}$C NMR (100 MHz, $CD_3OD$), 167.4, 154.2, 143.2, 137.3, 128.9, 127.0, 118.6, 30.8, 30.5, 27.5, 27.1, 25.7, 20.0 ppm. HRMS calcd for C15H19NO4S: (M-H): 308.0957, Found: 308.0953.

EXAMPLE 14

31. N-(4-fluorophenyl)sulfonyl-α-dehydrocyclohexylglycine

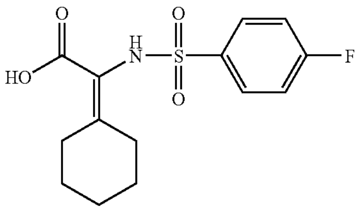

2-cyclohexyl-2-oxoethanoic acid (3.0 g, 19.2 mmol) was combined with p-toluenesulfonamide (2.70 g, 15.4 mmol) in toluene (21 mL) and diethyleneglycol diethyl ether (3 mL). MSA (0.10 mL, 1.5 mmol) was added, and this mixture was heated at reflux for 28 h, then cooled to rt. The resulting solids were mixed with EtOAc (35 mL) and $NaHCO_3$ (2.6 g) in water (60 mL), until all materials dissolved. The aqueous was separated, and the organics were washed with NaH $CO_3$ (0.40 g) in water (10 mL). The combined aqueous layer was then washed with EtOAc (20 mL). The aqueous layer was cooled to 0 C, then treated with HCl (12.1 N, 3.1 mL). The resulting solids were filtered and washed with water and dried to give 3.0 g of crude material. The solids were then recrystallized from toluene/methanol to give 2.8 g of white solid (58% yield).

mp 214-215° C. $^1$H-NMR (400 MHz, $CD_3OD$), d 7.83-7.88 (m, 2H), 7.23-7.29 (m, 2H), 2.61-2.65 (m, 2H), 2.21-2.24 (m, 2H), 1.55-1.59 (m, 4H), 1.41-1.46 (m, 2H); $^{13}$C NMR (100 MHz, $CD_3OD$), 167.2, 166.3, 163.7, 155.3, 136.5 (2 peaks), 129.9 (2 peaks), 118.3, 115.5, 115.3, 31.0, 30.5, 27.6, 27.2, 25.7 ppm. HRMS calcd for C14H15FNO4S: (M-H): 312.0706, Found: 312.0707.

EXAMPLE 15

32. N-toluenesulfonyl-α-dehydroaminobutyric acid

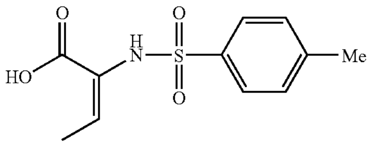

2-oxobutyric acid (10.0 g, 97.9 mmol) was combined with p-toluenesulfonamide (13.4 g, 78.4 mmol) and MSA (0.51 mL, 7.8 mmol) in toluene (70 mL) and diethyleneglycol diethyl ether (10 mL). This mixture was heated at reflux for 28 h, then cooled to rt. To the resulting mixture was added EtOAc (50 mL) and $NaHCO_3$ (13.1 g) in water (150 mL). Upon complete dissolution, the aqueous was separated, and the organics washed with $NaHCO_3$ (2.0 g) in water (50 mL). The combined aqueous layer was then washed with EtOAc (50 mL), then cooled to 0 C and treated with 12.1N HCl (16.0 mL). The product did not crystallize, so it was quickly extracted with EtOAc (150 mL). The organics were dried (MgSO4), and passed through silica-gel (150 mL) to remove dark color. The resulting organics were stripped to give 13.1 g of off-white solid. This was recrystallized from toluene/n- heptane, then again from toluene to give 9.1 g of white solid. Materials in the mother liquors were recrystallized from toluene to give an additional 2.6 g of material. Total yield was 11.7 g (59% yield).

mp 150.5-151.5° C. $^1$H-NMR (400 MHz, $CD_3OD$), d 7.69 (d, 2H, 20.8 Hz), 7.32 (d, 2H, 20.7 Hz), 6.92 (q, 1H, 17.8 Hz), 2.41 (s, 3H), 1.81 (d, 3H, 17.8 Hz); $^{13}$C NMR (100 MHz, $CD_3OD$), 165.8, 143.4, 138.9, 137.4, 128.9, 127.0, 126.8, 20.0, 13.3 ppm. HRMS calcd for C11H12NO4S: (M-H): 254.0487, Found: 254.0482.

EXAMPLE 16

33. N-toluenesulfonyl-α-dehydroleucine

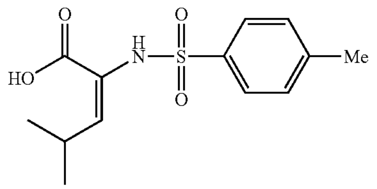

4-methyl-2-oxopentanoic acid, sodium salt (5.0 g, 32.9 mmol) was slurried in MTBE (25 mL) and cooled to 0 C, then HCl (12.1 N, 3.0 mL) was added. The resulting biphasic was warmed to rt, then saturated with $Na_2SO_4$. The inorganic solids were filtered and washed with MTBE (25 mL). The combined organics were stripped to give a light-yellow oil. This oil was dissolved in toluene (35 mL) and diethyleneglycol diethyl ether (5 mL) and p-toluenesulfonamide (4.5 g, 26.3 mmol) then methanesulfonic acid (0.17 mL, 2.6 mmol) were added. The resulting mixture was heated at reflux with Dean-Stark removal of water for 24 h, then cooled to 5 C. The resulting solids were mixed with EtOAc (75 mL) and $NaHCO_3$ (4.2 g) in water (100 mL), until all materials dissolved. The aqueous was separated, and the organics were washed with $NaHCO_3$ (0.50 g) in water (20 mL). The combined aqueous layer was then washed with EtOAc (25 mL). The aqueous layer was cooled to 0 C, then treated with HCl (12.1 N, 5.0 mL). The resulting oil was extracted into EtOAc (2×50 mL), then stripped to give a solid, a 10:1 mixture of olefin isomers by 1H-NMR analysis The solids were then recrystallized from toluene/hexanes to give 4.2 g of white solid (57% yield), as a single isomer.

mp 166.5-167.5° C. $^1$H-NMR (400 MHz, $CD_3OD$), d 7.69 (d, 2H, 20.8 Hz), 7.32 (d, 2H, 20.0 Hz), 6.56 (d, 1H, 26.9 Hz), 2.86-2.93 (m, 1H), 2.40 (s, 3H), 0.95 (d, 6H, 16.6 Hz); $^{13}$C NMR (100 MHz, $CD_3OD$), 166.3, 149.7, 143.4, 137.3, 128.9, 127.1, 123.5, 27.3, 20.6, 20.1 ppm. HRMS calcd for C13H16NO4S: (M-H): 282.0800, Found: 282.0805.

Synthesis of Racemic and Non-racemic N-sulfonyl amino acids

Racemic amino acid Derivatives

Racemic amino acids used for chiral HPLC analysis were prepared by one of two methods. The yields were not determined.

Method A. Racemic compounds 34, 35, 36, 37, 38, 41, were prepared by dissolving the corresponding DL-amino acid in water using NaOH (2 equiv.), then adding the sulfonyl chloride (1 equiv.). Upon completion of reaction, the mixture was acidified with HCl, and the products crystallized in high purity from water and recrystallized if necessary.

Method B. Racemic compounds 39, 40, 42 were prepared by hydrogenation of the corresponding dehydroamino esters in Methanol at room temperature, using 10% Pd/C (25 wt %), 40 psi H2. The reactions proceeded cleanly, in quantitative yield. The products were isolated by filtration through celite, then passing through silica-gel to remove polar impurities.

Non-Racemic amino acids

Non-racemic amino acids were prepared using the following method. The yields were not determined. Non-racemic, commercially available amino acid was slurried in acetone/water (1:1) at 0 C, then NaOH (2.0 N, 1 equiv.) was added to dissolve. Then diisopropyl ethyl amine (1.1 equiv.) was added, followed by the corresponding sulfonyl chloride (1.1 equiv.). The reaction was allowed to warm to rt, then the acetone was removed by rotary evaporation. The resulting water was diluted with water, then HCl (2N, 1 equiv.) was added. The pure derivatized amino acid was isolated from water, then crystallized or chromatographed to high-purity.

Data for Racemic and Non-racemic amino acid Derivatives

EXAMPLE 17

34. N-toluenesulfonyl valine

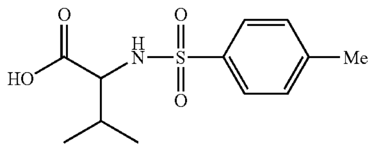

mp 149-150.5° C. $^1$H-NMR (400 MHz, $CD_3OD$), d 7.72 (d, 2H, 20.9 Hz), 7.33 (d, 2H, 21.7 Hz), 3.61 (d, 1H, 14.0 Hz), 2.41 (s, 3H), 1.99-2.04 (m, 1H), 0.94 (d, 3H, 17.0 Hz), 0.89 (d, 3H, 17.1 Hz); $^{13}$C NMR (100 MHz, $CD_3OD$), 172.8, 143.1, 137.7, 129.0, 126.8, 61.3, 30.9, 20.0, 18.1, 16.6 ppm. HRMS calcd for C12H16NO4S: (M-H): 270.0800, Found: 270.0803.

EXAMPLE 18

35. N-(4-OMe benzene)sulfonyl valine

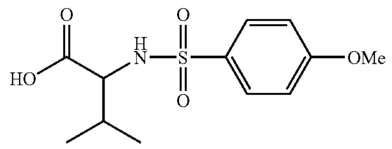

mp 116.5-117.5° C. $^1$H-NMR (400 MHz, $CD_3DO$), d 7.77 (d, 2H, 22.6 Hz), 7.02 (d, 2H, 22.5 Hz), 3.86 (s, 3H), 3.52 (d, 1H, 12.9 Hz), 3.32 (m, 1H), 0.94 (d, 3H, 17.0 Hz), 0.87 (d, 3H, 17.0 Hz); $^{13}$C NMR (100 MHz, $CD_3OD$), 174.7, 162.8, 132.1, 128.9, 113.6, 61.9, 54.7, 31.0, 18.4, 16.6 ppm. HRMS calcd for C12H16NO5S: (M-H): 286.0749, Found: 286.0746.

EXAMPLE 19

36. N-(4-F benzene)sulfonyl valine

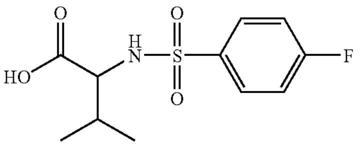

mp 132-133° C. $^1$H-NMR (400 MHz, $CD_3OD$), δ 7.90 (m, 2H), 7.25 (m, 2H), 3.65 (d, 1H, 14.0 Hz), 1.99-2.10 (m, 1H), 0.96 (d, 3H, 17.0 Hz), 0.90 (d, 3H, 17.1 Hz); $^{13}$C NMR (100 MHz, $CD_3OD$), 172.7, 166.1, 163.6, 137.0, 136.9, 129.7, 129.6, 115.6, 115.3, 61.3, 30.9, 18.2, 16.6 ppm. HRMS calcd for C11H13FNO4S: (M-H): 274.0549, Found: 274.0552.

EXAMPLE 20

37. N-(Benzyl)sulfonyl valine

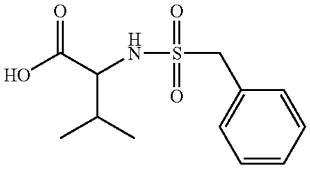

mp 120-121.5° C. $^1$H-NMR (400 MHz, $CD_3OD$), 7.42 (m, 2H), 7.34 (m, 3H), 4.31 (m, 2H), 3.75 (d, 2H, 13.0 Hz), 2.09 (m, 1H), 0.98 (d, 3H, 17.1 Hz), 0.91 (d, 3H, 17.1 Hz); $^{13}$C NMR (100 MHz, $CD_3OD$), 173.6, 130.8, 129.7, 128.2, 128.1, 61.8, 59.1, 31.1, 18.2, 16.8 ppm. HRMS calcd for C12H16NO4S: (M-H): 270.0800, Found: 270.0804.

EXAMPLE 21

38. N-(3-phenylpropylsulfonyl)valine

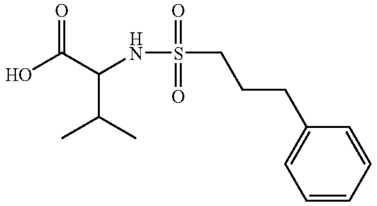

mp 151-152° C. $^1$H-NMR (400 MHz, $CD_3OD$), d 7.26-7.30 (m, 2H), 7.16-7.22 (m, 3H), 3.77 (d, 1H, 13.4 Hz), 2.98-3.02 (m, 2H), 2.71-2.75 (m, 2H), 2.03-2.20 (m, 3H), 1.0 (d, 3H, 17.0 Hz), 0.93 (d, 3H, 17.1 Hz); $^{13}$C NMR (100 MHz, $CD_3OD$), 173.6, 140.6, 128.0 (2 peaks), 125.7, 61.3, 52.1, 33.7, 30.7, 25.0, 18.3, 16.5 ppm. HRMS calcd for C14H20NO4S: (M-H): 298.1113, Found: 298.1112.

EXAMPLE 22

39. N-(toluenesulfonyl)cyclohexylglycine

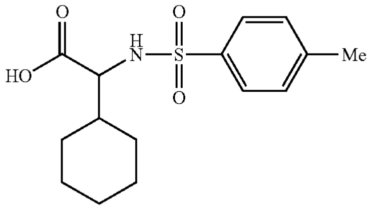

mp 182-184° C. $^1$H-NMR (400 MHz, $CD_3OD$), d 7.72 (d, 2H, 20.8 Hz), 7.33 (d, 2H, 20.1 Hz), 3.61 (d, 1H, 14.8 Hz), 2.41 (s, 3H), 1.56-1.75 (m, 6H), 0.97-1.28 (m, 5H); $^{13}$C NMR (100 MHz, $CD_3OD$), 172.7, 143.0, 137.7, 129.0, 126.8, 60.7, 40.4, 29.2, 27.9, 25.6, 25.5 (2 peaks), 19.9 ppm. HRMS calcd for C15H20NO4S: (M-H): 310.1113, Found: 310.1111.

EXAMPLE 23

40. N-(4-F benzenesulfonyl)cyclohexylglycine

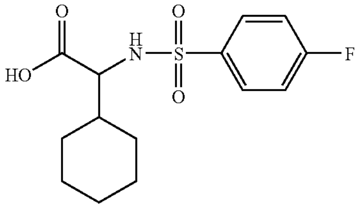

mp 143-145° C. $^1$H-NMR (400 MHz, $CD_3OD$), δ 7.87-7.91 (m, 2H), 7.23-7.27 (m, 2H), 3.64 (d, 1H, 14.8 Hz), 1.57-1.76 (m, 6H), 1.00-1.32 (m, 5H); $^{13}$C NMR (100 MHz, $CD_3OD$), 172.6, 166.1, 163.6, 137.0 (2 peaks), 129.7, 129.6, 115.3 (2 peaks), 60.8, 40.3, 29.3, 27.8, 25.6, 25.5 ppm. HRMS calcd for C14H17NO4S: (M-H): 314.0862, Found: 314.0861.

EXAMPLE 24

41. N-(toluenesulfonyl)aminobutyric acid

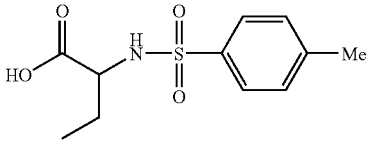

mp 133.5-135.5° C. $^1$H-NMR (400 MHz, $CD_3OD$), δ 7.73 (d, 2H, 16.6 Hz), 7.34 (d, 2H, 20.1 Hz), 3.72 (m, 1H), 2.41 (s, 3H), 1.72-1.77 (m, 1H), 1.59-1.66 (m, 1H), 0.90 (t, 3H, 18.3 Hz); $^{13}$C NMR (100 MHz, $CD_3OD$), 173.2, 143.1, 137.8, 129.0, 126.7, 57.0, 25.9, 20.0, 8.7 ppm. HRMS calcd for C11H14NO4S: (M-H): 256.0644, Found: 256.0648.

EXAMPLE 25

42. N-(toluenesulfonyl)leucine

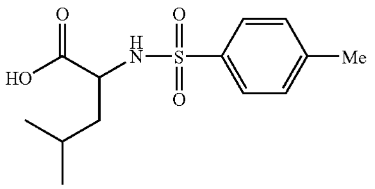

mp 122-123° C. $^1$H-NMR (400 MHz, $CD_3OD$), δ 7.72 (d, 2H, 20.8 Hz), 7.34 (d, 2H, 20.0 Hz), 3.80 (m, 1H), 2.41 (s, 3H), 1.66-1.78 (m, 1H), 1.48 (m, 2H), 0.89 (d, 3H, 16.8 Hz), 0.81 (d, 16.4 Hz); $^{13}$C NMR (100 MHz, $CD_3OD$), 174.3, 143.3, 137.9, 129.2, 126.9, 54.4, 41.8, 24.2, 21.9, 20.4, 20.2 ppm. HRMS calcd for C13H18NO4S: (M-H): 284.0957, Found: 284.0957.

EXAMPLE 26

(2R)-2-{[(4-Fluoro-3-methylphenyl)sulfonyl]amino}-N-hydroxy-2-(tetrahydro-2H-pyran-4-yl)acetamide

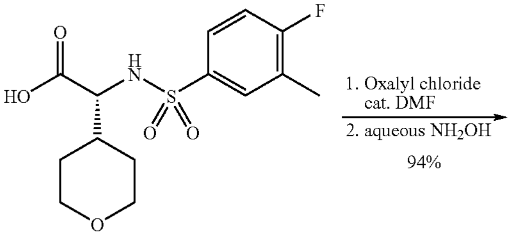

8
99.5% ee
<3 ppm Ru, Fe
Sulfonamide Acid

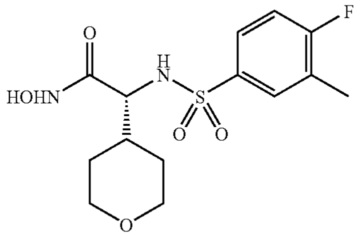

Sulfonamide acid 8 was dissolved in 3.2 L of THF (4 vol). This water level was high (KF=2400 μg/mL) due to water in the solid 8. More THF (4 L) was added and the solution was batch concentrated to the initial vol (KF=1200 μg/mL). A caustic scrubber was connected to the reaction flask. DMF (18.5 mL) was added, the solution was cooled over a −15° C. dry ice/acetone bath to 5° C. and 248 mL of oxalyl chloride was added from an addition funnel over 20 min at ~5° C. The mixture was allowed to age 2 h, after which the batch was cooled to −42° C. and 790 mL of aqueous 50 wt % $NH_2OH$ was poured in from an open neck. The resulting reaction was exothermic and the batch temperature rose to 35° C. quickly before drifting down. The mixture was diluted with 630 mL of water and 410 mL of conc HCl was added to adjust the pH to 4.5. EtOAc (9.5 L) was added along with 100 mL water and the mixture was warmed to 45° C. to dissolve the solids that were present. The mixture was transferred to an extractor, the aqueous layer was cut, and the organic layer was washed with 960 mL of water. The organic layer was passed through a pad of Solka floc and then batch concentrated to 4 L in a 22 L round bottom flask. Evaporation was continued with addition of 13 L of EtOAc to remove THF. A thick mixture of solids formed during this distillation and required ~9 L vol to maintain good mixing. The slurry was heated to 70° C. and aged for 3 h. n-Heptane (8.2 L) was added over 2 h, the mixture was aged for 1 h at 70° C. and allowed to cool and age overnight. The slurry (25° C.) was filtered (filter pot) rinsing with 4 L of 1:1 EtOAc/n-heptane. The solids were dried for 5 h under nitrogen and then were transferred to three trays and dried 2 days at 40° C. to afford 783 g (99.6 wt %, 99.9 A %, 94.4% yield) of product.

EXAMPLE 27

Formation of CBZ-enamide ester (3)

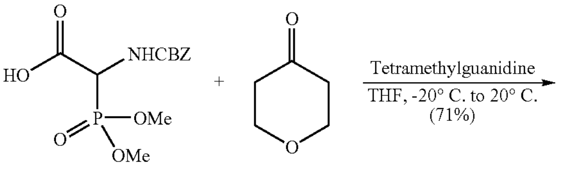

1
MW 331.26

2
MW 100.12

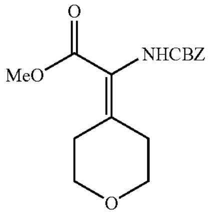

3
MW 305.33

Tetramethylguanidine (1.91 g, 16.6 mmol) was added to a solution of N-(benzyloxycarbonyl)-α-phosphonoglycine trimethyl ester 1 (5.00 g, 15.09 mmol) in anhydrous THF (7.5 mL) at −20° C. After stirring for 1 h at −20° C., a solution of tetrahydro-4H-pyran-4-one 2 (1.89 g, 16.6 mmol) in THF (2 mL) was added. The cooling bath was removed and the mixture was stirred at RT for 1 day. The assay yield was 82%. The reaction mixture was diluted with 25 mL of EtOAc and washed with 2x25 mL of 0.1N HCl and 50 mL of brine. The loss to washes was 1%. The organic layer was concentrated and the residue was dissolved in 20 mL of toluene at 60° C. Slow cooling to RT afforded a slurry, which was further cooled over an ice bath and aged 3 h. The solids were filtered and washed with 4 mL of cold toluene to afford after drying 3.27 g of CBZ-enamide ester 3 (71% yield) The mother liquor loss was 9%. The solids were recrystallized from toluene with 90% recovery of 3.

mp=112° C. $^1$H-NMR ($CDCl_3$, 400 MHz): δ 7.36-7.27 (m, br, 5H), 6.13 (s, 1H), 5.14 (s, 2H), 3.75 (m, br, 7H), 2.92 (m, 2H), 2.43-2.40 (t, 2H, J=11 Hz); $^{13}$C-NMR ($CDCl_3$, 100 MHz): δ 165.1, 154.9, 146.9, 136.0, 128.5, 128.3, 128.1, 119.5, 68.2, 67.9, 67.3, 51.9, 32.0. 31.2. Anal. Calcd for $C_{16}H_{19}NO5$: C, 62.94; H, 6.27; N, 4.59. Found: C, 62.77; H, 6.20; N, 4.47.

EXAMPLE 28

Asymmetric hydrogenation to CBZ-aminoester (4)

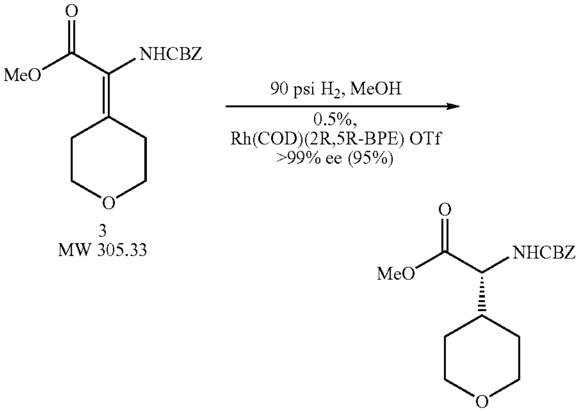

3
MW 305.33

4
MW 307.34

The CBZ-enamide 3 (5.00 g, 16.4 mmol) was dissolved in MeOH (180 mL, $N_2$ sparged to exclude oxygen) and degassed (vacuum/$N_2$ fill cycles). The catalyst, (+)-1,2-bis((2R,5R)-2,5-dimethylphospholano)ethane(cyclooctadiene)rhodium(I) trifluoromethanesulfonate (100 mg, 0.16 mmol, Strem cat#45-0171) was added under a $N_2$ blanket. The mixture was shaken in a Parr apparatus for 15 h under 45 psi $H_2$. The catalyst was filtered and the solvent was evaporated to afford 5.0 g (>95% uncorrected yield) of CBZ-aminoester 4 as a colorless oil. A 100 g scale-up run was done at 90 psi $H_2$ and afforded >99% ee.

Note: The use of pure CBZ-enamide ester 3 is required for successful hydrogenation.

$^{1}$H-NMR ($CDCl_3$, 500 MHz): δ 1.47 (m, 3H), 1.55 (m, 1H), 2.03 (m, 1H), 3.36 (m, 2H), 3.76 (s, 3H), 3.98 (m, 2H), 4.35 (m, 1H), 5.11 (s, 2H), 5.32 (d, J=9 Hz, 1H), 7.4 (m, 5H).

EXAMPLE 29

Hydrogenolysis to aminoester Salt (5)

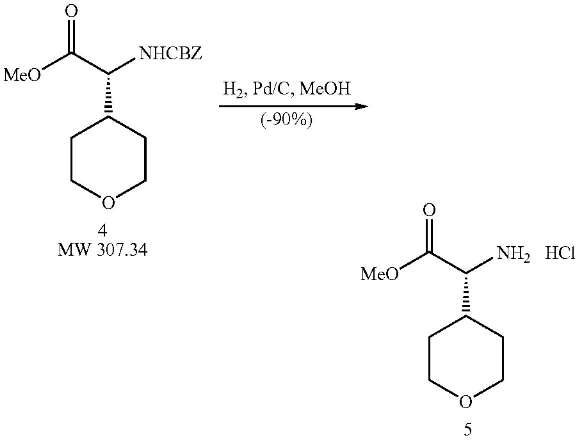

4
MW 307.34

5
MW 209.67

The aminoester 4 was hydrogenated in MeOH over Pd/C and the aminoester was isolated as its crystalline HCl salt 5.

mp=143° C. $^{1}$H-NMR ($d_6$ DMSO, 400 MHz): δ 8.81 (s, 3H), 3.83 (m, 3H), 3.73 (s, 3H), 3.22 (t, J=11 Hz, 2H), 2.10 (m, 1H), 1.57 (t, J=14 Hz, 2H), 1.45 (dq, J=4, 12 Hz, 1H), 1.26 (dq, J=4, 12 Hz, 1H). $^{13}$C-NMR ($d_6$ DMSO, 100 MHz): δ 28.2, 28.7, 36.4, 52.9, 56.5, 66.8, 66.9, 169.2. Anal. Calcd for $C_8H_{16}ClNO_3$: C, 45.83; H, 7.69; N, 6.68. Found: C, 45.38; H, 7.84; N, 6.47.

EXAMPLE 30

Sulfonyl chloride/primary sulfonamide synthesis

Step 1: Sulfonation to sodium sulfonate (7)

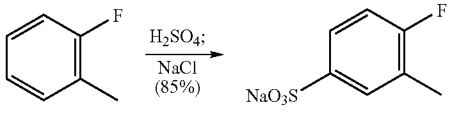

6
MW 110.13

7
MW 212.17

Concentrated sulfuric acid (80 mL, 1.47 mol) was added to a flask containing o-fluorotoluene 6 (55.07 g, 0.500 mol) at RT. The mixture was heated slowly to ~80° C. over 30 min with agitation (the reaction is exothermic and gradual heatup is recommended to prevent heatup >80° C., which results in a colored product). The resulting oil was agitated at 80° C. for 3 h until <0.7 A % of SM 6 remained. The reaction mixture was quenched with cold water (500 mL, the internal temperature rose to 110° C. briefly at the beginning of addition then quickly dropped to 50° C. after all water was added). Acetonitrile (55 mL) was added, followed by solid NaCl (135 g, 2.31 mol). The mixture was heated to 75° C. to dissolve all solids and was then cooled to 72° C. at which temperature seeds were added (100 mg of 7). Solids formed gradually at 70° C. The slurry was cooled to RT over 2 h and was cooled to <4° C. for 0.5 h. The solids were filtered, rinsed with 20% aqueous NaCl (165 mL), and dried in a 50° C. vacuum oven to afford 111.3 g (85% yield, 99.8 A %, 80.6 wt % purity) sodium sulfonate 7

Note: The regioisomer 7a was present at 1.5% and co-elutes with 7 in the HPLC assay.

7a

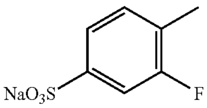

mp=decomp 370° C. $^{1}$H-NMR (400 MHz, $D_2O$): δ 2.23 (s, 3H), 7.10 (t, J=9.2 Hz, 1H), 7.54~7.63 (m, 2H). $^{13}$C-NMR (100 MHz, $D_2O$): δ 13.6 (d, J=1.9 Hz), 115.2 (d, J=23.4 Hz), 125.0 (d, J=9.4 Hz), 126.0 (d, J=18.5 Hz), 128.8 (d, J=6.1 Hz), 138.0 (d, J=3.2 Hz), 162.5 (d, J=248 Hz).

Step 2: Chlorination to sulfonyl chloride (8)

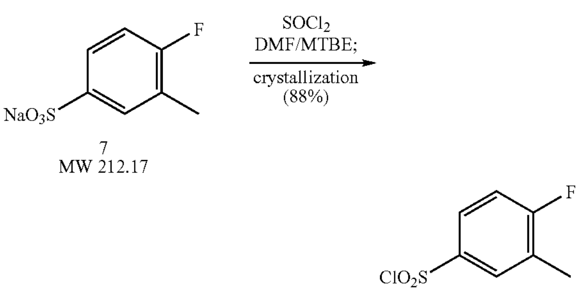

7
MW 212.17

8
MW 208.64

The sodium sulfonate 7 (79.0 g, 80.6 wt % pure, 300 mmol) was added to MTBE (474 mL) and DMF (7.9 mL) at RT. To the slurry was added $SOCl_2$ (53.8 g, 450 mmol). The mixture was warmed to 40° C. and agitated 3 h until <1.7 A % of SM 7 remained. The reaction was quenched with cold water (237 mL), agitated for 5 min, and was allowed to settle. The aqueous layer was cut and the organic layer was washed with 10% NaCl (2×237 mL) and was concentrated to afford the sulfonyl chloride 8 as a pale yellow oil (63.6 g, 1.5% region-isomer 8a). This was diluted in heptane (90 mL) and seeded at RT with 8 to afford a slurry. (Note: Alternatively, the solution of 8 in MTBE can be solvent-switched to heptane with <2% residual MTBE and concentrated to 90 mL volume). The slurry was cooled to <3° C. over 2 h (Note: Fast cooling results in solids precipitating on the walls of the flask). The solids were filtered and dried under vacuum at RT to afford 55.4 g (88% yield, >99.9 A %, 98.9 wt % purity) sulfonyl chloride 8. ML loss was 9%.

mp=36° C. $^1$H-NMR (400 MHz, $CDCl_3$): δ 2.40 (d, J=2.0 Hz, 3H), 7.22 (t, J=8.7 Hz, 1H), 7.87~7.94 (m, 2H). $^{13}$C-NMR (100 MHz, $CDCl_3$): δ 14.5 (d, J=3.2 Hz), 116.4 (d, J=24.6 Hz), 127.2 (d, J=9.8 Hz), 127.5 (d, J=19.2 Hz), 130.7 (d, J=6.8 Hz), 139.7 (d, J=3.2 Hz), 165.0 (d, J=258 Hz). Anal. Calcd for $C_7H_6ClFO_2S$: C, 40.30; H, 2.90; S, 15.37. Found: C, 40.41; H, 2.71; S, 15.48.

Step 3: Preparation of sulfonamide (11) from sulfonyl chloride (8)

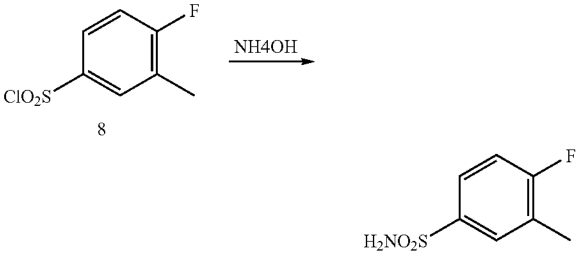

8

11

Oily sulfonyl chloride 2 (19.70 g, 94.2$^{wt}$ % pure, 88.9 mmol) from above slow reverse addition procedure was dissolved in 125 mL of MTBE. Ammonium hydroxide solution (28%, 16 mL) and water (16 mL) was added. The mixture was stirred for 1.5 h until HPLC showed no 2. $H_2SO_4$ (1 M, 40 mL) was added and aqueous layer was cut. Organic was washed with 50 mL of 10% $KHCO_3$, then with 50 mL of 10% brine. The organic solution was concentrated to 50 mL and the concentrate was heated to 45° C. Heptane (20 mL) was added at 45° C. The solution was seeded and a slurry formed. More heptane (80 mL) was added over 2 h at 45° C. The resulting slurry was cooled to RT over 1 h, then was cooled <5° C. and was aged at <5° C. for 20 min. Filtration afforded some crystalline solid and the cake was rinsed with 30 mL of 1:2 MTBE/heptane. After vacuum oven drying, 16.06 g of sulfonamide 7 was obtained as white crystalline solid. By HPLC, the solid was 99.6 A % and ~100$^{wt}$ % (vs. reference) pure. There was no regioisomer 7a in the product. The yield of 7 was 95% from 2.

EXAMPLE 31

Coupling to sulfonamide ester (9)

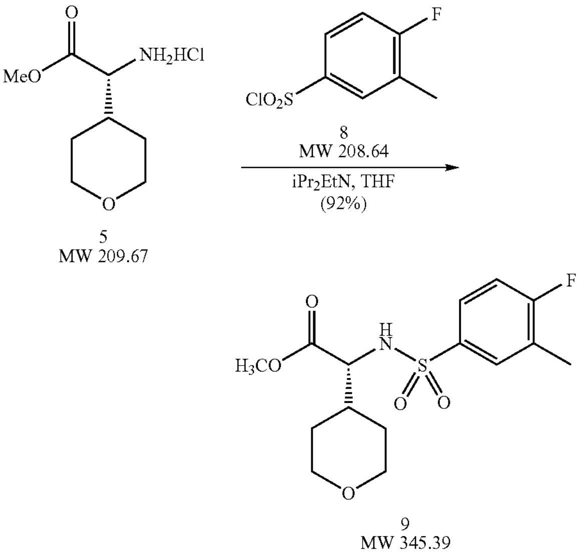

5
MW 209.67

8
MW 208.64

9
MW 345.39

The aminoester salt 5 (50 g, 238 mmol) was suspended in THF (300 mL), DIEA (87.2 mL, 501 mmol) was added, then a solution of sulfonyl chloride 8 (49.8 g, 238 mmol) in THF (170 mL) was added over 10 min (exothermed from RT to 37° C.). The mixture was stirred 13 h at 40° C. and then was allowed to cool and age overnight. The reaction mixture was diluted with IPAc (300 mL) and water (200 mL) and adjusted to pH 3-4 with 1N HCl (30 mL). The aqueous layer was cut and the organic layer was washed with water (200 mL). The organic layer was concentrated to 400 mL and was evaporated with IPAc (3×300 mL). The resulting slurry (420 mL) was heated to 82° C. to dissolve the solids and was cooled to 75° C. where crystallization was observed. The slurry was cooled at 13° C./h to RT, then heptane (840 mL) was added over ~2 h, and the slurry was stirred overnight. The solids were filtered and rinsed with 2:1 heptane/IPAc (60 mL) to afford after drying in a 40° C. oven 75.9 g (92% yield, 99.7 A % purity, >99% ee) of the sulfonamide ester 9.

mp=145° C. $^1$H-NMR ($d_6$ DMSO, 400 MHz): δ 8.31 (d, J=9 Hz, 1H), 7.68 (d, J=7 Hz, 1H), 7.60 (m, 1H), 7.33 (t, J=9 Hz, 1H), 3.79 (m, 2H), 3.63 (t, J=9 Hz, 1H), 3.37 (s, 3H), 3.17 (m, 2H), 2.28 (s, 3H), 1.80 (m, 1H), 1.48 (d, J=13 Hz, 1H), 1.26 (m, 2H), 1.16 (dq, J=4, 12 Hz, 1H). $^{13}$C-NMR ($d_6$ DMSO, 100 MHz): δ 14.4 (d, J=3.2 Hz), 28.8, 29.1, 37.3, 51.9, 60.6, 66.7, 67.0, 116.0 (d, J=23.8 Hz), 125.8 (d, J=18.6 Hz), 127.1 (d, J=9.5 Hz), 130.5 (d, J=6.3 Hz), 137.1 (d, J=3.2

Hz), 162.9 (d, J=250 Hz), 171.1. Anal. Calcd for $C_{15}H_{20}FNO_5S$: C, 52.16; H, 5.84; N, 4.06. Found: C, 52.21; H, 5.78; N, 4.00.

What is claimed is:

1. A process for making a compound of formula III or Formula IIIa:

Formula III

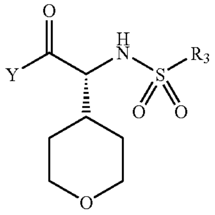

or

Formula IIIa

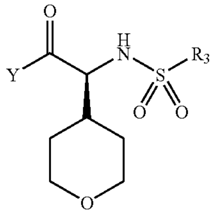

a pharmaceutically acceptable salt or mixture thereof, wherein:

$R_3$ represents $(CH_2)_nC_{6-10}$aryl, said aryl substituted with 2 groups of $R^a$;

$R^a$ represents $C_{1-6}$alkyl and halogen;

Z represents $S(O)_2$;

Y represents NHOH; and n is 0;

said process comprising:

(1) reacting a compound of formula IV:

Formula IV

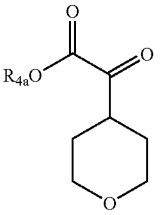

wherein $R_{4a}$ represents H, $C_{1-4}$alkyl, magnesium, lithium or sodium, with a compound of formula V:

Formula V

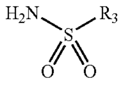

in the presence of an acid selected from the group consisting of methanesulfonic acid, pTsOH, CSA, $PhSO_3H$, phosphoric acids, TFA, AcOH, $H_2SO_4$, HCl and $POCl_3$;

(2) heating to a temperature of about 100° C. to about 125° C., for about one to about 30 hours, to produce a compound of formula VI:

Formula VI

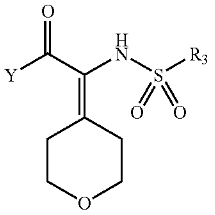

(3) asymmetrically hydrogenating a compound of formula VI in the presence of a metal catalyst and ligand to produce a compound of formula III or IIIa.

2. A process for making a compound of Formula III, Formula IIIa or mixture thereof:

Formula III

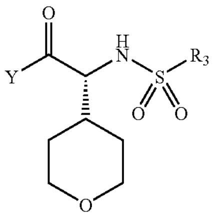

or

Formula IIIa

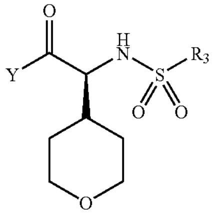

a pharmaceutically acceptable salt or mixture thereof, wherein:

$R_3$ represents $(CH_2)_nC_{6-10}$aryl, said aryl substituted with 2 groups of $R^a$;

$R^a$ represents $C_{1-6}$alkyl and halogen;

Z represents $S(O)_2$;

Y represents NHOH; and n is 0;

said process comprising:

(1) asymmetric hydrogenation of a compound of formula IX:

Formula IX

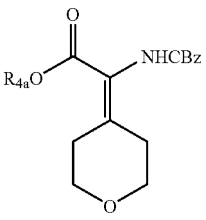

in the presence of a rhodium or ruthenium catalyst/ligand complex to produce a compound of formula IXa, IXb or a mixture thereof:

Formula IXa

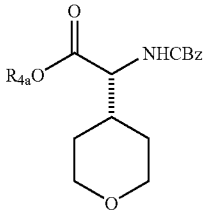

or

Formula IXb

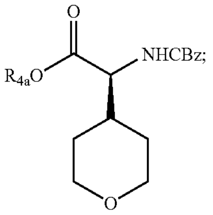

(2) hydrogenolysis of a compound of formula IXa, IXb or a mixture thereof in the presence of a palladium catalyst to produce a compound of formula VIII, VIIIa, a pharmaceutically acceptable salt or mixture thereof:

Formula VIII

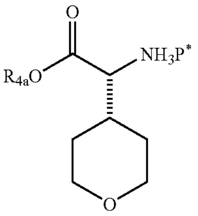

or

-continued

Formula VIIIa

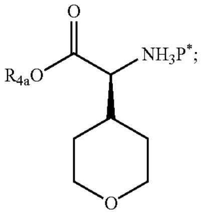

wherein P* is an acid and $R_{4a}$ represents H, $C_{1-4}$alkyl, magnesium, lithium or sodium;

(3) coupling the compound of formula VIII or VIIIa or mixture thereof with compound of formula X:

Formula X

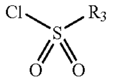

in the presence of a base selected from the group consisting of triethylamine, diisopropylethylamine, tri-n-butylamine, NaOH, LiOH, KOH, $NaHCO_3$, $Na_2CO_3$;

(4) hydrolyzing and purifying the coupled compound to produce a compound of formula III or IIIa.

3. A process according to claim 2, wherein the acid is selected from the group consisting of HCl, acetic acid, HI, HBr, TFA, PTSA, and $HBF_4$.

4. The process according to claim 1, wherein the compound of Formula III or Formula IIIa is (2R)-2-{[(4-Fluoro-3-methylphenyl)sulfonyl]amino}-N-hydroxy-2(tetrahydro-2H-pyran-4-yl)acetamide.

* * * * *